United States Patent [19]

Shor et al.

[11] Patent Number: 5,424,187

[45] Date of Patent: Jun. 13, 1995

[54] METHOD OF SCREENING FOR ARTERIAL CHLAMYDIAL GRANULOMA

[75] Inventors: Allan Shor, 76 Klip Street, Observatory Extension, Johannesburg 2000, South Africa; Cho-chou Kuo, Seattle, Wash.

[73] Assignees: Board of Regents of the University of Washington, Seattle, Wash.; Allan Shor, Johannesburg, South Africa

[21] Appl. No.: 898,905

[22] Filed: Jun. 12, 1992

[30] Foreign Application Priority Data

Jun. 14, 1991 [ZA] South Africa .................. 91/4565
May 21, 1992 [ZA] South Africa .................. 92/3699

[51] Int. Cl.$^6$ .................. C12Q 1/68; C12Q 1/00; G01N 33/53
[52] U.S. Cl. .................. 435/6; 435/4; 435/7.1
[58] Field of Search .................. 435/4, 6, 7.1

[56] References Cited

U.S. PATENT DOCUMENTS 5,008,186  4/1991  Grayston et al. .................. 435/7.36

FOREIGN PATENT DOCUMENTS

WO90/00061  1/1990  WIPO .................. A61K 39/118

OTHER PUBLICATIONS

Shor, A., J.G., Brunton, J.D. Cantrell, and G. E. H. van Sittert. A preliminary study of structures found in human coronary artery lesions. Electron Microscopic Society of South Africa 21:241–242, Dec. 1991.
Dictionary of Immunology. W J Herbert et al. eds. (1985) p. 89.
Dictionary of Microbiology and Molecular Biology, P. Singleton et al. eds (1991) p. 395.
Nevill, Woolf, "*Pathology of Atherosclerosis*", Butterworths Scientific Co., Ltd. pp. 1–2 and pp. 47–65 (1982).
Haust, M. D. The morphogenesis and fate of potential and early atherosclerotic lesions in man. *Human Pathology* 2: 1–29 (1971).
Kuo, C-C., E. Y. Chi, and J. T. Grayston. Ultrastructural study of entry of Chlamydia strain TWAR into HeLa cells. *Infect. Immun.* 56: 1668–1672 (1988).
Bocan, T. M. A. and J. R. Guyton. Human aortic fibrolipid lesions: Progenitor lesions for fibrous plaques, exhibiting early formation of the cholesterol-rich core. *Am. J. Pathol.* 120: 193–206 (1985).
Gerrity, R. G. The role of the monocyte in atherogenesis. I. Transition of blood-borne monocytes into cells in fatty lesions. *Am. J. Pathol.* 103: 181–190 (1981).
Gerrity, R. G. The role of the monocyte in atherogenesis. II. Migration of foam cells from atherosclerotic lesions. *Am. J. Pathol;.* 103: 191–200 (1981).
Gorstein, F. Ubiquitous smooth muscle cell. *Human Pathology* 20: 1035–1036 (1989).
Orekhov, A. N., E. R. Andreeva, A. V. Krushinsky, I. D. Novikov, V. V. Tertov, G. V. Nestaiko, A. Khasimov, V. S. Repin, and V. N. Smirnov. Intimal cells and atherosclerosis, *Am. J. Pathol.* 125: 402–415 (1986).
Parums, D. and M. J. Mitchinson. Demonstration of Immunoglobulin in the neighbourhood of advanced atherosclerotic plaques. *Atherosclerosis* 38: 211–216 (1981).
Ramshaw, A. L. and D. V. Parums. Immunohistochemical characterization of inflammatory cells associated with advanced atherosclerosis. *Histophatol.* 17: 543–552 (1990).
Manor, E. and I. Sarov. Fate of *Chlamydia trachomatis* in human monocytes and monocyte-derived macrophages. *Infect. Immun.* 54: 90–95 (1986).

(List continued on next page.)

*Primary Examiner*—Margaret Parr
*Assistant Examiner*—David Schreiber
*Attorney, Agent, or Firm*—Christensen, O'Connor, Johnson & Kindness

[57] ABSTRACT

Method of diagnosing arterial chlamydial granuloma by detecting in a biological sample both a first marker associated with *Chlamydia pneumoniae* and a second marker associated with arterial granuloma. Therapeutic composition for treating arterial chlamydial granulomatous disease, including an anti-*Chlamydia pneumoniae* agent and a granuloma inhibitor.

3 Claims, 20 Drawing Sheets

OTHER PUBLICATIONS

Hajjar, D. P. Virus-induced atherosclerosis: Herpesvirus infection alters aortic cholesterol metabolism and accumulation. *Am. J. Pathol.* 122: 62–70 (1986).

Melnick, J. L., E. Adam, and M. E. DeBakey. Special role of cytomegalovirus in atherogenesis. *JAMA* 263: 2204–2207 (1990).

Grayston, JT, Kuo CC, Campbell LA, Wang SP. *Chlamydia pneumoniae* sp. nov. for *Chlamydia* sp. strain TWAR. Int. J. Syst. Bacteriol. 1989; 39: 88–90.

Chi EY, Kuo, CC, Grayston T.J. Unique ultrastructure in Elementary Body of *Chlamydia* sp. strain TWAR. Int. J. Syst. Bacteriol. 1987; 169:3757–3673.

Grayston TJ, Campbell LA, Kuo CC, Mordhorst CH, Saikku P, Thom DH, Wang SP. A New Respiratory Tract Pathogen. *Chlamydia pneumoniae* Strain TWAR. J. Infect. Dis. 1990; 161: 618–625.

Saikku P, Mattila K, Nieminen MS, Huttunen JK, Leinonen M, Ekman MR, Mäkelä PH, Valtonen V. Serological evidence of an association of a novel *Chlamydia*, TWAR with chronic Coronary Heart Disease and Acute Myocardial Infarction. Lancet, 1988; 2: 983–985.

Thom DH, Wang SP, Grayston JT, Siscovick DS, Steward DK, Kronmal RA, Weiss NS. *Chamydia pneumoniae* strain TWAR antibody and angiographically demostrated coronary artery disease. Arteriosclerosis and Thrombosis 1991; 11: 547–551.

Kuo CC, Chen HH, Wang SP, Grayston T. Identification of New Group of *Chlamydia psittaci* Strains called TWAR. J. Clin. Microbiol., 1986; 24: 1034–1037.

Guyton JR, Klemp KF. The Lipid Rich Core Region of Human Atherosclerotic Fibrous Plaques. Am. T. Pathol., 1989; 134:705–717.

Sutton GC, Demakis JA, Anderson TO, Morrissey RA. Serologic evidence of a sporadic outbreak in Illinois of infection by Chlamydia (psittacosis–LGV agent) in patients with primary myocardial disease and respiratory disease. Am. Heart J 1971; 81: 597–607.

Grayston TT, Mordhorst CH, Wang SP. Childhood myocarditis associated with *Chlamydia tracomatis* infection. JAMA 1981; 246: 2823–2827.

Jones RB, Priest JB, Kuo CC. Subacute chlamydial endocarditis. JAMA 1982; 247: 655–658.

Marrie TJ, Harczy M, Mann OE, Landymore RW, Raza A, Wang SP, Grayston JT. Culture-negative endocarditis probaly due to *Chlamydia pneumoniae*. J. Infect Dis 1990; 161: 127–129.

Benditt EP, Barrett T, McDougall JK. Viruses in the etiology of atherosclerosis. Proc. Natl. Acad. Sci. USA. 1983; 80: 6386–6389.

Saikku P, Leinonen M, Tenkanen L, Linnanmaki E, Ekman MR, Manninen V, Manttari M, Frick MH, Huttunen JK, Chronic *Chlamydia pneumoniae* infection as a risk factor for coronary heart disease in the Helsinki Heart Study. Ann Int. Med 1992; 116:273–278.

Campbell LA, Perez-Melgosa M, Hamilton DJ, Kuo CC, Grayston JT, Detection of *Chlamydia pneumoniae* by polymerase chain reaction. J. Clin. Microbiol 1992;30:434–439.

Kuo CC, Grayston JT, A sensitive cell line, HL cells, for isolation and propagation of *Chlamydia pneumoniae* strain TWAR. J. Infect Dis 1990;162:755–758.

Kuo CC, Grayston JT, Factors affecting viability and growth in HeLa 229 cells of *Chlamydia* sp. strain TWAR. J. Clin. Microbiol. 1988;26:812–815.

Kuo CC, Cultures of *Chlamydia trachomatis* in mouse peritoneal macrophages: Factors affecting organism growth. Infect. Immun. 1978; 20:439–445.

Yong, EC, Chi EY, Kuo CC, Differential antimicrobial activity of human mononuclear phagocytes against the human biovars of *Chlamydia trachomatis*. J. Immunol 1987;139:1297–1302.

Chen WJ, Kuo CC, A mouse model of pneumonitis induced by *Chlamydia trachomatis*: Morphologic, microbiologic and immunlogic studies. Am J Pathol 1980;100:365–377.

Rothermel CD, Schachter J, Lavrich P, Lipsitz EC, Francus T, *Chlamydia trachomatis*-induced production interleukin-1 by human monocytes. Infect Immun 1989;57:2705–2711.

Kuo CC, Grayston JT, *In vitro* drug susceptibility of *Chlamydia* sp. strain TWAR. Antimicrob Agent Chemother 1988; 32:257–258.

Lipsky BA, Tack KJ, Wang SP, Kuo CC, Grayston JT, Ofloxacin treatment of a *Chlamydia pneumoniae* (strain TWAR) lower respiratory tract infections. Am. J. Med 1990;89:722–724.

Grayston, J. T., Kuo, C. C., Wang, S. P., Altman, J. A new *Chlamydia psittaci* strain, TWAR, isolated in acute respiratory tract infections. New. Engl. J. Med. 1986;315:161–168.

(List continued on next page.)

OTHER PUBLICATIONS

Kleemola, M., Saikku, P., Visakorpi, R., Wang, S.P. Epidemics of pneumonia caused by TWAR, A new chlamydia organism, in military trainees in Finland. J. Infect. Dis. 1988; 157:230–236.

Campbell, L. A., Kuo, C. C., Thissen, R. W. and Grayston, J. T. Isolation of a gene encoding a *Chlamydia* sp. strain TWAR protein that is recognized during infection of humans. Infect. Immun. 1989;57:71–75.

Ladany, S., Black, C. M., Farshy, C. E., Ossewaarde, J. M. and Barnes, R. C. Enzyme immunoassay to determine exposure to *Chlamydia pneumoniae* (Strain TWAR). J. Clin. Microbiol. 1989;27:2778–2783.

Fu, Y., Baumann, M., Kosma, P., Brade, L. and Brade, H. A synthetic glycoconjugate representing the genus-specific epitope of Chlamydial lipopolysaccharide exhibits the same specificity as its natural counterpart. Infect. Immun. 1992;60:1314–1321.

Stuart, E. S., Wyrick, P. B., Choong, J., Stoler, S. B., MacDonald, A. B. Examination of chlamydial glycolipid with monoclonal antibodies: cellular distribution and epitope binding. Immunol. 1991; 74: 740–747.

Karimi, S. T., Schloemer, R. H. and Wilde, C. E. Accumulation of infected cells. Infect. Immun. 1989; 57: 1780–1785.

Brade, L., Holst, O., Kosma, P., Zhang, Y-X., Paulsen, H. Krausse, R., and Brade, H. Characterization of murine monoclonal and murine, rabbit, and human polyclonal antibodies against Chlamydial lipopolysccharide. Infect. Immun. 1990; 58: 205–213.

Shor, A., Kuo, C. C., Patton, D. L., Fukushi, H., and Campbell, L. A. Detection of *Chlamydia pneumoniae* in the coronary artery atheroma plaque. 1992. Amer. Soc. Microbiol. Abstract #D-67, p. 107, General Meeting, New Orleans, La.

Bobo, L., Coutlee, F., Yolken, R. H., Quinn, T., and Viscidi, R. P. Diagnosis of *Chlamydia trachomatis* cervical infection by detection of amplified DNA with an enzyme immunoassay. J. Clin. Microbiol. 1990, 28: 1968–1973.

Holland, S. M., Taylor, H. R., Gaydos, C. A., Kappus, E. W. and Quinn, T. C. Experimental infection with *Chlamydia pneumoniae* in nonhuman primates. Infect. Immun. 1990, 58:593–597.

Bell, T. A., Kuo, C.-C., Wang, S. P. and Grayston, J. T. Experimental infection of baboons (*Papio cynocephalus anubis*) with *Chlamydia pneumoniae* strain 'TWAR'. J. Infection 1989, 19: 47–49.

Koskenvuo, M. and Romanov, K., Lancet 1989, i: 158, and Saikku, P., Leinonen, M., Mattila, K., Ekman, M. R., Nieminen, M. S., Makela, P. H., Huttunen, J. K., and Valtonen, V., Lancet 1989, i: 158.

Leinonen, M., Linnanmaki, E., Mattila, K., Nieminen, M. S., Valtonen, V., Leirisalo-Repo, M., and Saikku, P. Circulating immune complexes containing Chlamydial lipopolysaccharide in acute myocardial infarction. Microbial Pathogenesis 1990, 9: 67–73.

Thom, D. H., Wang, S-P., Grayston, J. T., Siscovick, D. S., Stewart, D. K., Weiss, N. S., and Kronomal, R. A. The association between *Chlamydia pneumoniae* strain TWAR antibody and angiographically demonstrated coronary artery disease. Circulation 1991, 83: 736.

Thom, D.H., Grayston, J.T., Wang, S-P., Kuo, C.C. and Altman, J. *Chlamydia pneumoniae* strain TWAR, *Mycoplasma pneumoniae*, and viral infections in acute respiratory disease in a University student health clinic population. Amer. J. Epidemiol. 1990, 132: 248–256.

TABLE 1: CASE DESCRIPTIONS AND FINDINGS OF CORONARY ARTERY

| Case No. | Age (yr) | Sex | Race | Cause of death | Stage of Atheroma | Detection of C. pneumoniae | |
|---|---|---|---|---|---|---|---|
| | | | | | | Electron microscopy | Immunoperoxidase stain |
| I | 26 | M | Indian | Trauma | Early | present | negative |
| II | 25 | M | White | Trauma | Early | present | postive |
| III | 26 | M | White | Epilepsy | Late | present | positive |
| IV | 44 | M | Black | Undetermined natural cause | Late | present | positive |
| V | 44 | M | Black | Trauma | Late | present | positive |
| VI | 31 | M | Black | Trauma | Late | present | positive |
| VII | 25 | M | Black | Trauma | Complicated | present | negative |

5 controls: No atheroma present and were negative for immunoperoxidase stain except for cases5 which showed heavy haemosiderin deposition in the subintima with a non specific attachment of the stain to this material.

Atheroma: Early, fatty streak; late, fibrolipid plaque; complicated, degenerate interstitial tissue and early calcification.

*Fig. 1.*

TABLE 2: CASE DESCRIPTIONS AND FINDINGS OF CORONARY ARTERY CONTROL GROUP

| Case No. | Age (yr) | Sex | Race | Cause of death | Stage of Atheroma | Detection of C. pneumoniae | |
|---|---|---|---|---|---|---|---|
| | | | | | | Electron microscopy | Immunoperoxidase stain |
| 1 | 30 | M | Black | Trauma | None | Not done | negative |
| 2 | 39 | M | Black | Trauma | None | Not done | negative |
| 3 | 44 | M | Black | Asphyxia | None | Not done | negative |
| 4 | Not Stated | M | Black | Stabwounds | None | Not done | negative |
| 5 | 26 | M | Black | Trauma | None | Not done | negative |

5 controls: The controls were taken from the left conronary artery or left anterior descending branch. These arteries showed no atheroma macroscopically or on light microscopic examination. The controls were negative for immunoperoxidase stain except for case 5 which showed heavy haemosiderin deposition in the subintima with a non-specific attachment of the stain to this material.

Fig.2.

Fig. 4A.
Fig. 4B.
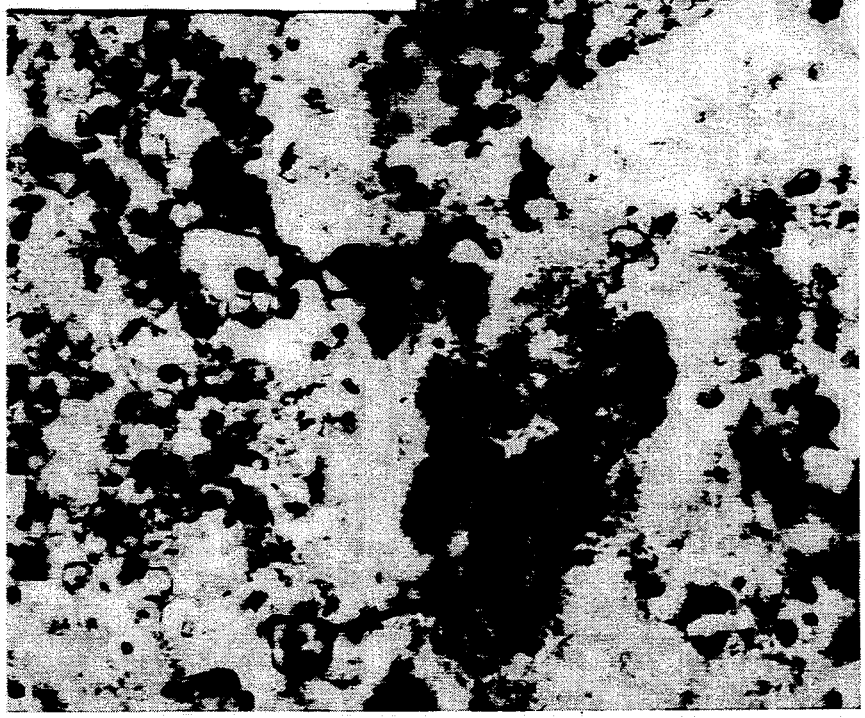

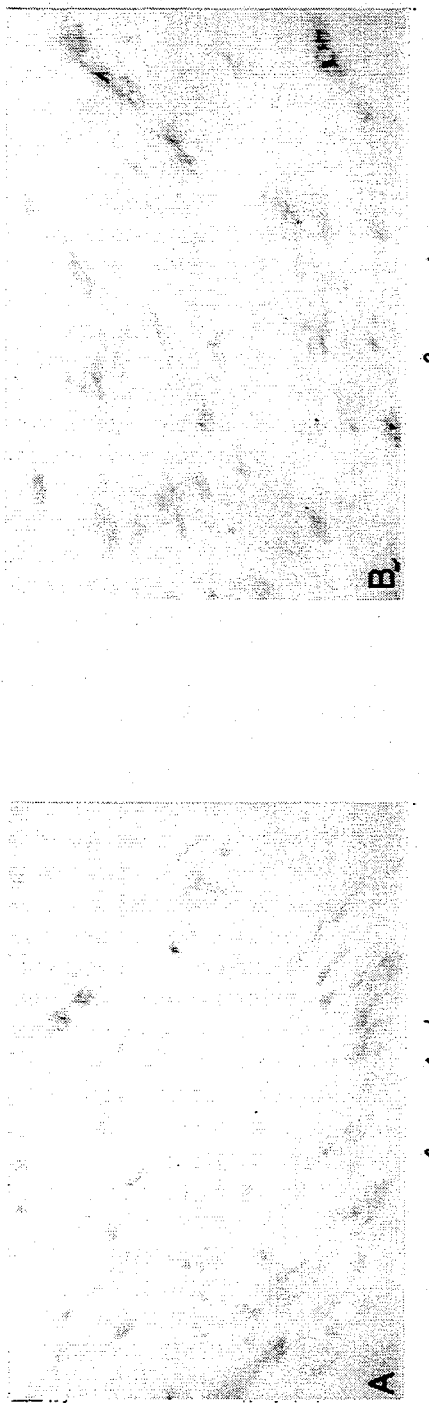
Fig. 6A.
Fig. 6B.
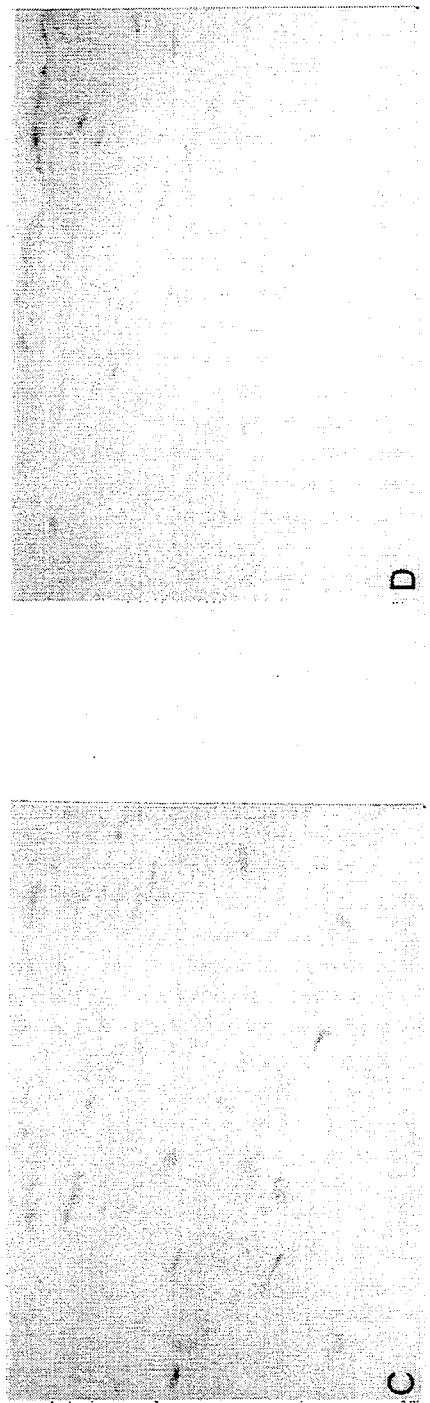
Fig. 6C.
Fig. 6D.

Detection of *Chlamydia pneumoniae* organisms in coronary artery atheromas by immunoperoxidase stain and polymerase chain reaction.

| Immunoperoxidase* | polymerase chain reaction | | | Total |
|---|---|---|---|---|
| | + | − | NT† | |
| + | 6‡ | 4 | 5 | 15 |
| − | 5 | 14 | 2 | 21 |
| Total | 11 | 18 | 7 | 36 |

* Separate tissues were used for two tests

† Not tested

‡ Number of cases

*Fig. 7.*

```
  2 GTGTAATTAGGCATCTAATATATATTAAAGAAGGGGATCTTCGGACCTTT  51
  2 ..................................................  51
                                                        226
177 ...A.GT............A.C............................ 101
 52 CGGTTGAGGAAGAGTTTATGCGATATCAGCTTGTTGGTGGGGTAAAAGCC  101
 52 ..............................................TG.. 276
227 ........G.....C...G............................... 151
102 CACCAAGGCGATGACGTCTAGGCGGATTGAGAGATTGACCGCCAACACTG  151
102 ..................................................  326
277 T........TT....................................... 201
152 GGACTGAGACACTGCCCAGACTTCTACGGGAGGCTGCAGTCGAGAATCTT  201
152 ...................................A..............  376
327 ...................................A.............. 251
202 TCGCAATGGACGAAAGTCTGACGAAGCGGCGCCGCGTGTGTGATGAAGGC  251
202 ...................................A..............  426
377 ...................................A.............. 301
252 CTTAGGGTTGTAAAGCACTTTCGCCTGGGAATAAGAGAGATTGGCTAATA  301
252 ..................................................  476
427 TC.......................T........................ 351
302 TCCAATCGATTTGAGCGTACCGGGTAAAGAAGCACCGGCTAACTCCGTGC  351
302 ..................................................  526
477 ..............A................................... 401
352 CAGCAGCTGCGGTAATACGGAGGGTGCTAGCGTTAATCGGATTTATTGGG  401
352 ..................................................  576
527 .................................................. 451
402 CGTAAAGGGCGTGTAGGCGGAAAGGAAAGTTAGATGTTAAATTTTGGGGC  451
402 ..........................................C.......  626
577 .................................................. 501
452 TCAACCCCAAGTCAGCATTTAAAACTATCTTTCTAGAGGATAGATGGGGA  501
452 ..........................................G......A..  676
627 ........C......C...T.............................. 551
502 AAAGGGAATTCCACGTGTAGCGGTGAAATGCGTAGATATGTGGAAGAACA  551
502 ..................................................  726
677 .................................................. 601
552 CCAGTGGCGAAGGCGCTTTTCTAATTTATACCTGACGCTAAGGCGCGAAA  601
552 ..................................................  776
727 ................................C................. 651
602 GCAAGGGGAGCAAACAGGATTAGATACCCTGGTAGTCCTTGCCGTAAACG  651
602 ..................................................  826
777 .................................................. 701
652 ATGCATACTTGATGTGGATGGTCTCAACCCCATCCGTGTCGGAGCTAACG  701
652 .....................T...............T............  876
827 .............A....T....T.......................... 751
702 TGTTAAGTATGCCGCCTGAGGAGTACACTCGCAAGGGTGAAACTCAAAAG  751
702 ..................................................  926
877 C................................................. 801
752 GATTGACGGGGGCCCGCACAAGCAGTGGAGCATGTGGTTTAATTCGATGC  801
752 ..................................................  976
927 A................................................. 852
802 AACGCGAAGGACCTTACCTGGACTTGACATGTATTTGACAACTGTAGAAAT  852
802 ..........................................CG.G.C..  1027
977 .........A.......G................................
```

*Fig. 8.*

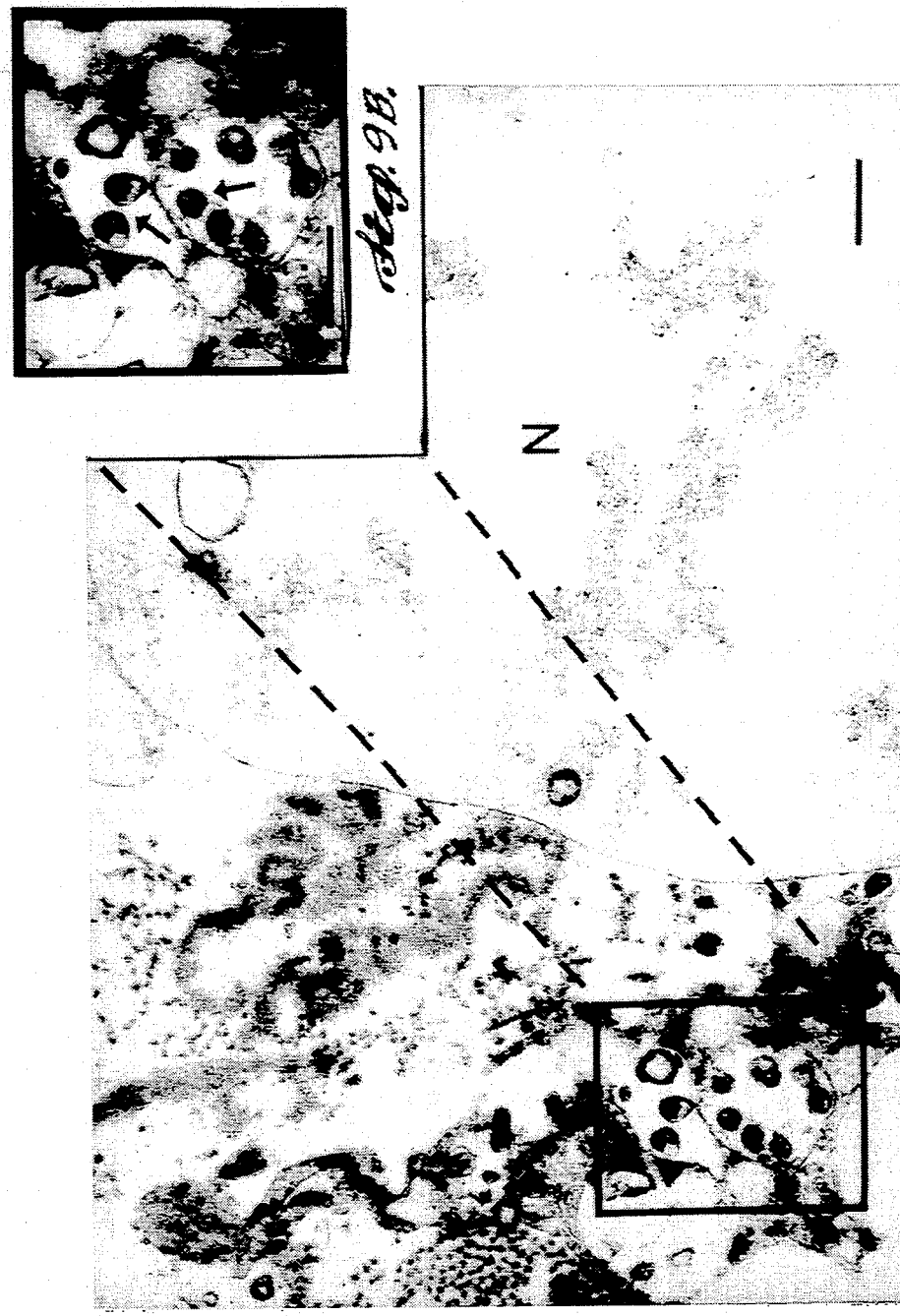

METHOD OF SCREENING FOR ARTERIAL CHLAMYDIAL GRANULOMA

This invention was made partly with government support under Public Health Service research grant AI-21885 awarded by the National Institutes of Health. The United States government has certain rights in the invention.

FIELD OF THE INVENTION

This invention relates to diagnosis and treatment of granulomatous disease in *Chlamydia pneumoniae*-infected arterial tissues.

BACKGORUND OF THE INVENTION

*Chlamydia pneumoniae* strain TWAR is a recently identified third species of Chlamydia that is unique based on serological, morphological, and DNA sequence homology (2,8; see the appended Citations). Humans are reportedly the sole host of *C. pneumoniae*.

Chlamydia are obligate intracellular bacteria. *C. trachomatis* and *C. pneumoniae* are human pathogens, while *C. psittaci* is an animal pathogen (1,18) which may incidentally infect humans. *C. pneumoniae* causes respiratory infections, while *C. trachomatis* causes mainly oculogenital infections. The primary syndrome caused by infection of humans with the arian strains of *C. psittaci* is a pneumonia known as psittacosis or ornithosis. The major clinical manifestations of *C. pneumoniae* infection are pneumonia, bronchitis, pharyngitis, and sinusitis (3,11). *C. pneumoniae* infection has been associated with about 10% of community-acquired pneumonia. The infections are geographically widespread. Antibody prevalence studies have shown that virtually everyone is infected with *C. pneumoniae* at some time and that reinfection is common.

Ultrastructurally the TWAR elementary body has a unique pear-shape and a large periplasmic space, in contrast to the typically round elementary bodies of *C. trachomatis* and *C. psittaci* (2). In addition, small electron-dense bodies of undetermined function are seen in the periplasmic space of TWAR elementary bodies. TWAR undergoes the same developmental cycle as other chlamydia, namely, infectious elementary bodies enter the cell and differentiate into reticulate bodies that undergo a series of divisions by binary fusion, with formation of reticulate bodies that mature to elementary bodies through an intermediate-form stage (2). Small outer membrane blebs are also sometimes seen.

U.S. Pat. No. 5,008,186, which is incorporated herein by reference, discloses methods for detecting *C. pneumoniae*, utilizing monoclonal antibodies directed against an antigenic determinant of the TWAR strain of chlamydia. A representative monoclonal antibody for this purpose is produced by the cell line RR 402 which has been deposited at the American Type Culture Collection under accession No. HB 9109.

Sero-epidemiological studies have reported that TWAR infection may be widespread in the human population, and antibodies have been reported in 40 to 60% of adults. Antibodies are uncommon in children under 8 years of age, and the incidence rises sharply in older children and young adults, reaching a plateau in incidence in persons of greater than 30 years of age. TWAR is reportedly a common cause of pneumonia and certain other acute respiratory infections (3,40,41).

Tetracyclines and macrolides are reportedly effective in treating *Chlamydial pneumoniae* respiratory infections.

Serological studies have reported an increase in antibody titers specific for *C. pneumoniae* and *C. trachomatis* in patients with myocarditis (3,12). In Finland, antibodies to TWAR were reported in 50% of patients with chronic coronary heart disease and in 68% of patients with acute myocardial infarction, as compared with an incidence of 17% in a control population (4,19). Thom et al. 1991 (5) reported results of a case-control study in which a relative risk of 2.0 for coronary artery disease was recorded among subjects with high titers of anti-TWAR IgG antibodies, when compared with control subjects having low titers of anti-TWAR and based on angiographically diagnosed coronary artery disease.

International Patent Publication No. WO 90/00061 describes methods for the treatment and diagnosis of coronary heart disease. This disclosure is based on the foundation that chlamydial infections, especially Chlamydia TWAR infections, play a significant role in the pathogenesis of coronary heart disease. The disclosed methods involve drug treatment and screening of or testing for presence of chlamydia or chlamydial antibodies. Also disclosed are pharmaceutical preparations for treating chlamydial infections in coronary heart disease.

Thus, a tenuous linkage between the presence of antibodies to *Chlamydia pneumoniae* and coronary heart disease has been suggested. However, the presence of circulating antibodies in such a large proportion of the human population is problematic for monitoring either the course or extent of a chlamydial infection, i.e., because the presence of antibodies is only indicative of an encounter sometime in life with an antigen. No evidence of chlamydial infection of heart or vascular tissue has previously been reported.

SUMMARY OF THE INVENTION

A new chlamydial disease is described herein, namely, arterial chlamydial granuloma resulting from infection of cells in the arterial wall with *Chlamydia pneumoniae* TWAR organisms. Chlamydial infection was demonstrated by transmission electron microscopy, and was confirmed by localizing chlamydial genus- and species-specific antigens, and *C. pneumoniae*-specific nucleic acids, at sites of arterial granuloma.

The invention provides a method of diagnosing arterial chlamydial granuloma, by detecting in a biological sample both a first marker associated with *Chlamydia pneumoniae* and a second marker associated with arterial granuloma. The first marker is, for example, a *C. pneumoniae* organism detected by electron microscopy, or a *C. pneumoniae* antigen detected by immunohistochemical staining or immunoassay with a *C. pneumoniae*-specific antibody or other binding partner, or a *C. pneumoniae*-specific nucleotide sequence detected by nucleic acid hybridization with a *C. pneumoniae*-specific probe, or a *C. pneumoniae* lipid detected by HPLC. The second, arterial granuloma-associated marker is, for example, selected from among macrophage foam cells, fibrolipid deposits, and intimal smooth muscle cell necrosis detected by electron microscopy, or the second marker is an intimal smooth muscle-specific antigen detected by immunoassay, or a granuloma-associated marker detected by immunoassay.

The invention also provides therapeutic compositions for treating arterial chlamydial granuloma, including an anti-*Chlamydia pneumoniae* agent and a granuloma inhibitor. Representative anti-*C. pneumoniae* agents for this purpose include tetracycline, erythromycin, clarithromycin, axithromycin, ofloxacin, sparfloxacin, and tamafloxacin. Representaive granuloma inhibitors include macrophage cytokine inhibitors, lymphokine inhibitors, anti-inflammatory quinolones, corticosteroids, and prednisone. The anti-*C. pneumoniae* agent and the granuloma inhibitor may be the same chemical compound, preferably a quinolone.

The subject therapeutic composition is typically provided in combination with a written protocol for administration of the therapeutic composition for treatment of arterial chlamydial granuloma to a patient in need of such treatment. A first category of such patients exhibit acute arterial restriction, in which case the written protocol directs intravenous administration of an amount of the anti-*Chlamydia pneumoniae* agent effective to substantially inhibit the spread of chlamydial infection into healthy arterial tissues following surgical removal of the restriction. A second category of patients exhibit nonacute arterial restriction; here the written protocol directs coadministration over at least 2 to about 8 months of an amount of the anti-*Chlamydia pneumoniae* agent sufficient to substantially inhibit growth of *C. pneumoniae* organisms, and an amount of the granuloma inhibitor sufficient to substantially inhibit the granulomatous process. A third category of patients are at risk of developing arterial chlamydial granulomatous disease. This category includes patients having a chronic chlamydial lung infection and patients having a serum marker profile selected from among: a serum titer of greater than about 1:64 of antibodies specific for *C. pneumoniae*; circulating *C. pneumoniae* organisms; a *C. pneumoniae* marker; and a circulating intimal smooth muscle cell antigen or a granuloma marker and circulating *C. pneumoniae* organisms or a *C. pneumoniae* marker. The written protocol for treating this third category of patients includes prophylactic coadministration of an amount of the anti-*Chlamydia pneumoniae* agent sufficient to substantially inhibit growth of *C. pneumoniae* organisms, and an amount of the granuloma inhibitor. Sufficient to substantially inhibit the granulomatous process.

BRIEF DESCRIPTION OF THE DRAWINGS

FIG. 1 as discussed in Example 1, below, details relevant clinical information concerning patients #I-VII, the pathological stage of granuloma, the electron microscopic evidence of *Chlamydia pneumoniae* infection, and confirmation of *C. pneumoniae* infection by immunoperoxidase staining of selected histological sections from atheromatous lesions.

FIG. 2 as discussed in Example 1 details relevant clinical information concerning control subjects #1–5.

FIG. 3 as discussed in Example 1 presents a composite photomicrograph taken at 40 power magnification of a selected histological section of the coronary artery of patient #III cut lengthwise. Arterial chlamydial granulomatous disease is manifest as a fibrolipid plaque, with a central lipid-rich core. The results of immunohistochemical staining and electron microscopy studies on adjacent thin sections of this artery are shown in FIGS. 4 and 5, respectively.

FIG. 4 as discussed in Example 1 shows an electron micrograph at 10,000× for FIG. 4A (and 25,000× for FIG. 4B) of the central lipid-rich core of the fibrolipid plaque shown in FIG. 3. (Bar=500 nm.) The micrograph shows that the central lipid-rich core of the fibrolipid plaque contains numerous vesicles that have the electron microscopic size and morphological features of *C. pneumoniae* TWAR organisms (arrows).

FIG. 5 as discussed in Example 1 shows a photomicrograph taken at 400× of a histological section that has been immunoperoxidase stained with antibody specific for Chlamydia (i.e., CF-2 genus specific monoclonal antibody, although similar staining was also observed with RR-402 TWAR-specific monoclonal antibody). The area shown in this photomicrograph is located at the periphery of the central lipid-rich core shown in FIG. 3; and positive immunoperoxidase-staining Chlamydia-infected cells are located in this region.

FIG. 6 as discussed in Example 2 shows a photomicrograph of a histological section reacted with Chlamydia-specific antibody and stained with immunoperoxidase to reveal the presence of TWAR organisms. FIG. 6A shows staining with Chlamydia genus-specific monoclonal antibody CF-2. FIG. 6B shows staining of *C. pneumoniae* with species-specific monoclonal antibody RR-402. FIG. 6C shows lack of staining with a control monoclonal antibody (i.e., normal ascites fluid). FIG. 6D shows lack of staining of a normal control artery by Chlamydia-specific monoclonal antibody CF-2.

FIG. 7 as discussed in Example 2 details the results of immunoperoxidase and PCR studies detecting *C. pneumoniae* in coronary artery granulomas.

FIG. 8 as discussed in Example 2 shows regions of nucleotide sequence from *C. pneumoniae* (cpn) (SEQ. ID. NO. 2) which correspond with nucleotide sequences amplified by PCR methods from the arterial tissues of case #7 (case 7) (case 7; SEQ. ID. NO. 1) infected with *Chlamydia pneumoniae*. Dots indicate the identified nucleotide was identical to that of the respective portion of the *C. pneumoniae* nucleotide sequence. Nucleotide sequence of Chlamydia psittaci (cps) (SEQ. ID. NO. 3) is also exhibited for comparison.

FIGS. 9A and 9B as discussed in Example 2 show transmission micrographs of a foam cell (macrophage) in chlamydial-diseased arterial tissue that contains *C. pneumoniae* TWAR organisms. The region of the micrograph enclosed in a box (in FIG. 9A) is enlarged slightly in FIG. 9B, where the arrows point to *C. pneumoniae* TWAR organisms.(N=nucleus).

FIGS. 10A and 10B as discussed in Example 2 show other transmission micrographs of a foam cell (macrophage) from chlamydial-diseased arterial tissue that contains *C. pneumoniae* TWAR organisms. The region of the FIG. 10A micrograph enclosed in a box is enlarged in FIG. 10B to show *C. pneumoniae* TWAR organisms in the endosomes of the foam cell. (FC=foam cell; N=nucleus)

FIG. 11 shows further enlargement of the same endosomal region of foam cells infected with *C. pneumoniae* that is shown in FIG. 10B. The micrograph shows the typical *C. pneumoniae* pear-shaped elementary bodies.

FIG. 12 as described in Example 3 shows arterial lesion with central necrosis and tissue reaction enclosed in square.

FIG. 13 as described in Example 3 is a higher power photomicrograph that shows granuloma cells, giant cells, and inclusion bodies of *Chlamydia pneumoniae* (marked "A" in the micrograph).

FIG. 14 as described in Example 3 is a photomicrograph showing a granulomatous reaction and inclusion bodies ("A").

FIG. 15 as described in Example 3 is a photomicrograph showing patchy intimal smooth muscle cell necrosis with a "moth-eaten" appearance of the cells and also oedema (marked by arrows).

FIG. 16 as described in Example 3 is a photomicrograph showing superficial monocyte/macrophage infiltrate in reaction to the smooth muscle cell necrosis. Early foam cell formation is indicated by the arrow.

FIG. 17 as described in Example 3 is a photomicrograph showing a smooth muscle cell with vacuoles ("1") containing pear-shaped bodies showing a periplasmic space and outer membrane blebs ("2"). (Original magnification 35,000×. A bar=200 nm.)

FIGS. 18A and 18B as described in Example 3 are photomicrographs showing intimal smooth muscle cells containing reticulate bodies ("1") and elementary bodies ("2"). (Original magnification of FIG. 18B is 20,000×.)

FIG. 19 as described in Example 3 is a photomicrograph showing fragments of intimal smooth muscle cells containing attached TWAR organisms.

FIG. 20A and 20B as described in Example 3 are photomicrographs showing elementary bodies (arrows) in interstitium and in relation to cholesterol ("1") and collagen bundles ("2").

DETAILED DESCRIPTION OF THE PREFERRED EMBODIMENT

A new chlamydial disease is described herein, namely, arterial chlamydial granuloma resulting from infection of cells in the arterial wall with *Chlamydia pneumoniae* TWAR organisms. Chlamydial infection was demonstrated by transmission electron microscopy, and was confirmed by a) immunohistochemical techniques (i.e., localizing chlamydial genus- and species-specific antigens in sites of infection) and b) isolation and nucleotide sequencing of *C. pneumoniae* nucleic acids from the sites of arterial granuloma.

Two routes of arterial infection are considered likely based on the present findings: 1) spread of TWAR infection from the lungs to sites of arterial trauma via infected wandering mononuclear phagocytes, i.e., macrophages; and 2) primary infection of arterial intimal smooth muscle cells with TWAR organisms, followed by subsequent infection of interstitial cells and tissue-infiltrating macrophages. The chlamydial infection results in a chronic granulomatous disease with macrophage and lymphocyte infiltration, multinucleate giant cells, foam cells (macrophages), focal tissue necrosis, and overlying fibrosis. Chlamydial arterial infection is manifest as a chronic clinical disease course. Fibrosis that is formed by the host to "wall off" the chlamydial infection creates additional tissue bulk that narrows the arterial lumen. Tissue necrosis from arterial chlamydial granuloma results in weakening of the arterial wall with the eventual formation of lesions that may progress to aneurysms.

Patients with arterial chlamydial granuloma are distinguished from patients with other forms of arterial disease by the presence of TWAR organisms, TWAR antigens, TWAR nucleic acid, and granulomatous disease at the sites of arterial narrowing or lesions. Patients with arterial chlamydial granuloma are distinguished diagnostically from patients with other forms of disease by at least one of the following criteria:

a) TWAR organisms in biopsy (or postmortem) histological specimens;

b) the presence of arterial narrowing and any three of the following four indicia of infection: (1) anti-TWAR antibodies, (2) circulating chlamydial lipids, antigens, or nucleic acids, (3) circulating intimal smooth muscle cell antigens, and (4) elevated circulating levels of cytokines secreted by activated macrophages (e.g., TNF, IL-1);

c) the concurrent localization of TWAR organisms by imaging (e.g., with radiolabeled monoclonal antibody imaging agents) at sites of arterial narrowing identified by angiography; and d) isolation of nucleic acid from a sample of an arterial plaque, and demonstration of either (1) hybridization under stringent conditions with TWAR nucleic acid, or (2) amplification of the arterial nucleic acid by PCR followed by nucleotide sequencing of the arterial nucleic acid and sequence comparison to confirm greater than 60% nucleotide sequence homology with a TWAR nucleotide sequence over a stretch of at least 15 nucleotide bases.

*Chlamydia pneumoniae*-specific imaging agents and methods are disclosed for identifying, e.g., during angiography, granulomatous lesions infected with TWAR organisms. Diagnostic processes and reagents are disclosed for monitoring the course and extent of arterial chlamydial granulomatous disease by monitoring chlamydial lipids released into circulation by infected intimal smooth muscle cells. In one method, a radiolabeled lipid precursor, e.g., diacylglycerol, is introduced into a patient; after a suitable period of time serum samples are collected, and HPLC is used to identify the levels of radiolabeled chlamydial lipids. In another method, immunoassays to measure the levels of granuloma cytokines (e.g., macrophage cytokines such as TNF and IL-1) are used to monitor arterial chlamydial infection. The latter granuloma cytokine diagnostic assays are useful for assessing the efficacy of anti-chlamydial agents administered systemically or locally at the lesion site.

Therapeutic processes are provided to control the spread of arterial chlamydial granuloma by local delivery of anti-chlamydial agents during surgical procedures (e.g., catheter procedures). The delivery of anti-chlamydial agents to arterial tissues damaged by surgery (e.g., following balloon angioplasty) can prevent spread of chlamydial infection to the traumatized vessel walls.

Therapeutic compositions and protocols are disclosed for treatment of arterial chlamydial granuloma with an anti-inflammatory agent (i.e., inhibitory to the granulomatous process) in combination with an anti-chlamydial drug (i.e., an antibiotic). In one protocol, an anti-inflammatory compound (e.g., a corticosteroid, prednisone, or quinolone) is coadministered with an anti-chlamydial drug (e.g., erythromycin). In another protocol, an inhibitor of granuloma cytokines (e.g., a TNF, IL-1, FGF, or PDGF inhibitor) is administered in combination with an anti-chlamydial drug (e.g., erythromycin). The therapeutic composition(s) are typically administered over a period of several months, and efficacy is monitored by determining the extent of chlamydial granulomatous disease in the infected arterial tissues, as disclosed herein.

Definitions

"Anti-chlamydial agent" refers to agents such as antibiotics, specific anti-TWAR antibodies, and the like that are capable of inhibiting the growth of a TWAR organism in a host cell.

"Anti-inflammatory agent" refers to those agents commonly so classified, e.g., corticosteroids, prednisone, quinolones (e.g., pentoxyfilline), and the like.

"Arterial chlamydial granuloma" and "arterial chlamydial granulomatous disease" are terms used interchangeably to refer to those arterial diseases characterized by chlamydial infection in the intima of arterial walls. Infected cells in the intima may include macrophages, intimal smooth muscle cells, and interstitial cells residing within an arterial wall. Infection of those cells with the TWAR organism is characterized by a histological pattern of granulomatous disease. Sites of infection with the TWAR organism may be identified, e.g., in serial histological sections stained with hematoxylin and eosin, by identifying sections containing a focal macrophage infiltrate and verifying the presence of the TWAR organism in macrophages, smooth muscle cells, and interstitial cells in such sections, e.g., using methods described in Example 1 below.

"Atherosclerosis" as used herein refers generally to changes in the intima of arteries characterized histologically by focal accumulations of lipids, complex carbohydrates, blood cells, and blood products, with fibrous deposits and calcium deposits. The key processes are thought to involve: a) proliferation of smooth-muscle cells within the arterial intima and elaboration of extracellular connective tissue elements such as collagen and elastin by those cells; and b) accumulation of intracellular and extracellular lipid, most of which reportedly is derived from plasma lipids (Woolf, 1982). Atherosclerosis is a generalized disease involving the intima of large and medium arteries such as the aorta, common iliac artery, femoral, popliteal, tibial and other arteries supplying the legs, the renal arteries, mesenteric and coeliac arteries and other abdominal arteries, pulmonary arteries, coronary arteries, innominate, carotid arteries, vertebral arteries, and cerebral arteries. "Atheroma" refers generally to a single atherosclerotic lesion in an artery. Pursuant to the present disclosure, at least some of these generally recognized atherosclerotic lesions (36) are now known result from arterial chlamydial granulomatous disease.

"Chlamydia" refers to the genus of obligate intracellular bacteria so named and well known. Chlamydiae develop and multiply in the cytoplasm of mammalian host cells within membrane-bound vesicles, called inclusions. Three developmental forms of chlamydia have been recognized. The elementary body is an extracellular form which is infectious. The reticulate body is an intracellular vegetative and multiplying form which is not infectious. The intermediate form is a transitional form which is observed when the reticulate body transforms into the elementary body.

"Chlamydia TWAR organism," "TWAR," and "TWAR organism" are terms used interchangeably to refer to *Chlamydia pneumoniae* bacteria. (*Chlamydia pneumoniae* is known as TWAR because of the laboratory identifying letters for the first two isolates: TW-183 and AR-39.) The species *Chlamydia pneumoniae* is differentiated from the other two species of Chlamydia, *C. trachomatis* and *C. psittaci,* by ultrastructural morphology of the elementary body, DNA homology, and serology. The elementary body of *Chlamydia pneumoniae* is pear-shaped, while other chlamydial elementary bodies are round. The DNA homology is less than 10% between the species. The organisms can be identified using a TWAR-specific monoclonal antibody, such as RR-402 and TT-205, and routine immunohistochemical procedures. *Chlamydia pneumoniae* is a recognized human respiratory pathogen which causes 5 to 10% of community-acquired pneumonia, bronchitis, and sinusitis.

"Granuloma" and "granulomata" refer interchangeably to focal sites of chlamydial infection in the arterial vessel wall characterized histologically by macrophage and lymphocyte infiltration, appearance of multinuclear giant cells, foam cells (macrophages filled with lipid droplets), tissue necrosis, fibrosis, and accumulation of lipids. Granulomas are tumor-like masses or nodules of granulation tissue and actively growing fibroblasts and capillary buds. Granuloma is a term well known in the art of chronic inflammatory diseases; and the histological features of granulomas are generally associated with infectious diseases such as *Mycobacterium tuberculosis, Mycobacterium leprae,* syphilis, and lymphogranuloma venereum, or invasion by a nonliving foreign body. The sites of arterial chlamydial granulomatous disease, as described herein, share certain common histological features, and clinical pattern of chronic disease, with those characteristics of other granulomatous diseases.

"Granuloma cytokine" refers to the products of intimal smooth muscle cells, macrophages, foam cells (macrophages), and multinucleate giant cells in sites of arterial chlamydial granulomatous disease. Granuloma cytokines are identifiable in the supernatant cultures of explanted arterial plaques that are infected with *C. pneumoniae* and include, for example, TNF, IL-1, PDGF, and the like.

"Granuloma cytokine inhibitor" refers to inhibitors of cytokines produced by macrophages, smooth muscle cells, and the like at sites of intimal smooth muscle infection by chlamydia, e.g., TNF, IL-1, PDGF, FGF, and the like.

"Granulomatous lesion" refers to certain more advanced forms of granulomatous arteries that are characterized by a patchy distribution of cells with focal areas of intimal smooth muscle cell necrosis. The intracellular inclusions visible by electron microscopy in granuloma cells (i.e., macrophages, smooth muscle cells, and interstitial cells) include diffuse intracytoplasmic small granular bodies, i.e., caused by the intracellular infection with chlamydia, and the presence of *C. pneumoniae* organisms, i.e., visible as typical pear-shaped elementary bodies with reticulate and intermediate forms.

"Granuloma inhibitor" refers to agents that inhibit the granulomatous process and/or inhibit the formation of a granuloma.

"Inhibit the granulomatous process" refers to agents capable of either inhibiting granuloma formation (see below), or capable of reversing an ongoing granulomatous process. Representative inhibitors include agents capable of: inhibiting growth of *C. pneumoniae* in smooth muscle cells or macrophages (e.g., antibiotics, agents inhibiting vesicle formation in cells required for chlamydial replication, and the like); or inhibiting necrosis in sites of *C. pneumoniae* infection (e.g., agents neutralizing toxins released by dead and dying cells, such as free radical inhibitors or superoxide dismutase inhibitors, TNF inhibitors, and the like); or inhibiting release of *C. pneumoniae* from infected cells (e.g., using cellular cytoskeletal inhibitors to inhibit budding of chlamydia from the cell membrane); and/or reducing the fibrolipid mass of the granuloma (e.g., agents inhibiting *C. pneumoniae* lipid metabolism).

"Substantially inhibiting the granuloma process" refers to inhibiting one or more events required for granuloma formation and development by at least 30%, preferrably by 60%, and most preferrably by greater than 90%. Examples of such events required for granuloma formation include: activation of a lymphocyte to produce a lymphokine; activation of a macrophage to produce a cytokine; synthesis of a lymphokine or a macrophage cytokine; recruitment of a blood lymphocyte or monocyte into a site of a granuloma; and activation of fibroblast proliferation and extracellular matrix secretion associated with fibrosis.

"Inhibiting granuloma formation" refers to a subclass of the inhibitors of the granulomatous process that are agents capable of preventing the formation of a granuloma. Representative examples include: agents capable of either inhibiting entry of C. pneumoniae into smooth muscle cells or macrophages (e.g., by blocking cellular receptors utilized for entry by chlamydia); and agents preventing specifically immune lymphocytes and activated macrophages from entry into arterial sites of C. pneumoniae infection (e.g., soluble chlamydial antigens blocking T-cell receptors, cytokine receptor antagonists inhibiting T-cell and macrophage activation, and the like).

"Immune complex disease" refers to those diseases characterized by detectable levels of circulating antigen-antibody complexes, e.g., detectable by their ability to bind and activate complement proteins such as C1q, C4, C2, and C3. Immune complex diseases are also characterized by their ability to bind to tissue and cellular receptors for the Fc portion of immunoglobulin, and activation fragments of C4 (e.g., C4b, C4bi, and the like) and C3 (e.g., C3b, C3bi, C3d-e, and the like). Immune complex deposition occurs in basement membrane sites of arterial circulation, e.g., in the renal glomerulus, with subintimal electron-microscopic-dense deposits adjacent to the basement membrane or underlying adventicia. Antigen-antibody complexes can injury tissues or organs where they localize. The pathogenesis of immune complex may be divided into at least three phases: formation of the circulating complexes, deposition of complexes in the walls of blood vessels in various parts of the body, and production of tissue injury.

"Intimal smooth muscle cell" refers to those cells present in the intimal layer of arteries that are further characterized histologically by their elongated shape, the presence of intracellular myofibrils, and the synthesis of intimal smooth muscle-specific proteins.

"Interstitium" refers to that portion of the intima of arterial tissues characterized by the presence of connective tissue elements, e.g., collagen and ground substance.

"Macrophage" refers to blood- and tissue-derived monocytes (also known as mononuclear phagocytes and wandering phagocytes) which enter the intima and are triggered in that location by chlamydial infection to develop phagocytic and other properties of activated macrophages.

"Marker associated with *Chlamydia pneumoniae*" refers to a polypeptide, lipid, glycolipid, carbohydrate, glycoconjugate, or nucleic acid that is detectable intracellular or extracellular in a *Chlamydia pneumoniae* organism isolated from an arterial chlamydial granuloma, or an organism isolated from tissue culture growth in an intimal smooth muscle cell, a macrophage, or another suitable tissue culture host cell.

"Intimal smooth muscle cell specific antigen" refers to an antigen found in intimal smooth muscle cells at a higher level than in other types of muscle cells.

"Prognostic levels" of a marker associated with *C. pneumoniae* or a granuloma refers to concentrations of the subject marker in the bodily fluid or tissue that are higher than background and predictive of a clinical condition, e.g., the presence of a granulomatous lesion.

"Acute arterial restriction" refers to narrowing of an artery that is judged by a practitioner to be an acute condition, e.g., possibly worthy of surgical intervention or aggressive drug therapy.

"Nonacute arterial restriction" refers to narrowing of an artery that is judged by a practioner not to be an acute condition, e.g., not worthy of surgical intervention or aggressive drug therapy.

"Substantially inhibiting spread of chlamydial infection" is used in the context of an agent capable of inhibiting spread of *C. pneumoniae* infection from a first cell to a second cell by at least about 30%, preferably by about 60%, and most preferably by greater than 90%. In a representative tissue culture assay, duplicate cultures of *C. pneumoniae*-infected cells are established, one as a control and the second as a test. The anti-*Chlamydia pneumoniae* agent is added to the test culture, and the numbers of chlamydial organisms in the culture are determined at various suitable times thereafter. An agent that substantially inhibits spread of chalmydial infection sufficient to inhibit the growth of the about 30% to about 90% or more of the chlamydial TWAR organisms in the test culture as compared with the control culture.

"Coadministration" refers to administration of two agents to a subject within an interval of time such that both agents are present in the bodily fluids or tissues of the subject for at least 10 minutes to many hours.

"Written protocol" refers to a set of recommendations to a medical practitioner for use of an agent(s) to treat or diagnose an arterial chlamydial infection, e.g., directions for use readable from a written or printed text or from an electronic medium.

Diagnostics

The invention provides methods for diagnosing arterial chlamydial granulomas by detecting in a biological sample both a marker associated with chlamydia and a marker associate with granuloma. The subject methods are useful both ex vivo and in vivo for diagnosing arterial chlamydial granulomatous disease. Illustrative ex vivo assays employ biological fluids (e.g., serum, plasma, bronchio-alveolar lavage fluids, and the like) and tissue samples (e.g., peripheral blood leukocytes; biopsy specimens obtained using surgical procedures including angioplasty and other catheter procedures).

Illustrative ex vivo assays for detecting chlamydia-associated markers in biological fluids include: immunoassay methods (e.g., to detect antigens using immunoassays, or immunohistochemical assays such as described in Examples 1-3, below); PCR methods (e.g., PCR to amplify *C. pneumoniae* nucleic acids, such as described in Example 2, and combined with dot-blot or other assays to detect the amplified nucleic acid); and HPLC methods (e.g., to identify characteristic *C. pneumoniae* lipids released from arterial granulomas). Other illustrative ex vivo assays include electron microscopy (i.e., to detect TWAR organisms as described in Examples 1-3), immunohistochemical staining (i.e., to detect TWAR antigen with anti-*C. pneumoniae* specific binding partners (e.g., see Examples 1-3), or in situ tissue hybridization with nucleotide probes (i.e., to detect *C. pneumoniae* nucleic acids).

The detection steps, i.e., detection of a first marker associated with chlamydia and a second marker associated with granuloma, may be performed in a single assay format, i.e., in the same assay, or in one or more separate assay formats. In a representative single assay format, an immunoassay is provided in which a capture antibody specific for smooth muscle cells or macrophages is used to immobilize TWAR organisms that are bound to fragments of cellular debris and membranes. After washing away unbound antigens, a detect antibody is employed that is specific for *C. pneumoniae*.

Granulomatous disease is a cell-mediated immune (CMI) response to infection involving specific immune T-cells and macrophages. CMI is conveniently tested using T-cell activation assays (e.g., lymphocyte blastogenesis assays using $^3$H-thymidine incorporation, short-term in vitro IL-2 production and assay by immunoassay, and the like) or skin testing (e.g., in a manner similar to a tuberculin skin test with PPD or tuberculin). Those skilled in the art will recognize that measurements of CMI may more properly reflect the status of an ongoing chronic granulomatous disease, i.e., arterial chlamydial disease, than serological tests for antibody or antigen. The subject ex vivo assays to detect chlamydia-associated markers and granuloma-associated markers also include cellular assays for determining and monitoring immune status, e.g., specific immune assays to examine T-cell activation (e.g., $^3$H-thymidine incorporation) in response to Chlamydia-genus and species-specific antigens (e.g., assays using peripheral blood leukocytes, lymphocytes, and subpopulations of cells prepared therefrom); as well as CMI-status (e.g., using cell sorting to determine the ratio of CD4+ helper to CD8+ killer cells).

Illustrative in vivo assays include diagnostic imaging (e.g., such as described in Example 6), skin testing for Chlamydia-specific CMI and the like, and the use of biosensor catheter probes with surface indicator substances, e.g., Chlamydia-specific binding partners conjugated with fluorophores whose quenching or signal wavelength shifting can be used for detecting chlamydial markers in situ in arteries.

For detecting arterial chlamydial granulomas, representative markers associated with *C. pneumoniae* include polypeptides (e.g., as described in references 44-45), carbohydrates, glycoconjugates (e.g., as described in reference 46), glycolipids (e.g., as described in reference 47), lipids (e.g., such as described in references 48-49), and nucleic acids. Such markers are typically associated with the chlamydial cell surface or cytoplasm in the arterial granuloma or following release from the lesion site.

Representative markers associated with granulomas include polypeptides, carbohydrates, lipids, and nucleic acids: namely, macrophage cytokines (e.g., IL-1, TNF, PDGF, and the like), macrophage activation-specific marker enzymes and antigens (e.g., 5' nucleotidase, glucuronidase, and the like), intimal smooth muscle cell degradation fragments (e.g., nucleic acids, myosin, myofibril antigens, and the like), markers for fibroplasia (e.g., FGF, EGF, extracellular matrix components such as collagen and proteoglycans, and intracellular matrix components such as cytokeratins and the like), and markers for endothelial cells and platelets that are activated by the granulomatous process (e.g., endothelial cell growth factors, PF4, and the like). Representative markers of arterial chlamydial granulomatous disease in microscopic assays include the presence in thin sections of foam cells, fibrolipid deposits, and include smooth muscle cell necrosis.

The invention provides methods for in vivo detection of chlamydial infection in arteries using diagnostic imaging methods. For instance, a $^{99m}$Tc-labeled anti-Chlamydia specific binding partner (or NMR-labeled specific binding partner) that is specific for a *Chlamydia pneumoniae*-associated marker may be delivered systemically or injected locally, e.g., via a catheter. Arterial tissues that react positively with the imaging agent may represent different stages in the infectious process, i.e., infected but pre-granulomatous or infected and granulomatous.

The invention also provides methods for in vivo detection of chlamydial infection at sites of arterial granulomatous disease that are associated with arterial lumen narrowing. Lumenal obstruction is commonly detected by angiographic methods using an X-ray opaque dye that is frequently introduced with a catheter into the artery of interest. Pursuant to the present disclosure, it is highly desirable in such a catheter protocol to introduce a diagnostic imaging agent either along with the contrast agent or shortly thereafter. For instance, a $^{99m}$Tc-labeled anti-Chlamydia specific binding partner (or NMR-labeled specific binding partner) may be used that is directed to a *Chlamydia pneumoniae*-associated marker. In this manner patients that have arterial chlamydial infection can be identified by the coincidence of lumenal narrowing (e.g., in X-ray) and chlamydial marker (e.g., in a gamma camera image of the same site). An illustrative example of a diagnostic imaging procedure is provided in Example 6. Patients with arterial chlamydial infection so diagnosed can be treated appropriately to prevent the spread of their arterial disease during surgical procedures (see Examples 7 and 8, below).

Therapeutic Agents

The therapeutic agent is generally administered to a patient in high doses for a period of typically two weeks and thereafter repeatedly over a length of several months until reversal of arterial chlamydial granulomatous disease is observed. Reversal of disease may be manifest as decreased narrowing of the effected artery, decreased levels of granuloma cytokines, decreased levels of chlamydial antigens (or lipids) in circulation.

Preferred therapeutic agents include, but are not limited to, antibiotics acting to inhibit or kill Chlamydia, e.g., tetracyclines, erythromycins, clarithromycins, azithromycin, and quinolones (e.g., ofloxacin, sparfloxacin, temafloxacin), and the like. Particularly preferred are agents that concentrate in macrophages and that inhibit growth of Chlamydia in macrophages, e.g., azithromycin, sparfloxacin, clarithromycin, and the like.

Delivery systems preferably target macrophages and intimal smooth muscle cells in arterial tissues that are chlamydia-infected. Representative delivery systems include anti-chlamydial agents encapsulated in particulate drug delivery systems targeted for macrophage phagocytosis, e.g., liposome encapsulation or silica-coated, and delivery methods similar to those utilized for targeting HIV-1 infection (42).

Particularly preferred therapeutic agents are classes of chemical compounds selected for both antichlamydial granuloma-inhibiting activities. Quinolones are considered to represent one such class of compounds since they are immunosupressive (e.g., in neutrophil chemotaxis and lymphocyte activation assays) and are also active in inhibiting the growth of C. pneumoniae in tissue culture.

Patients that may benefit from therapy may be divided into the following categories based on their clinical presentation:

Category I patients have acute arterial restriction or obstruction in which case intravenous medication is recommended with an amount of anti-chlamydial agent effective to prevent spread of chlamydial infection into healthy arterial tissues following surgical removal of the restriction or obstruction;

Category II patients have nonacute arterial obstruction, in which case medication is recommended over at least 2 to about 8 months with an amount of anti-chlamydial agent sufficient to stop growth of TWAR organisms, and an amount of granuloma inhibitor sufficient to inhibit or reverse granulomatous disease; and Category III patients are at risk of developing arterial chlamydial granulomatous disease, in which case prophylactic medication is recommended with an amount of anti-chlamydial agent sufficient to stop growth of TWAR organisms, and an amount of granuloma inhibitor sufficient to inhibit or reverse granulomatous disease. Such patients at risk include subjects having a chronic chlamydial lung infection, or patients having a serum marker profile selected from among: a serum titer of greater than about 1:64 of antibodies specific for Chlamydia pneumoniae; circulating TWAR organisms, antigens, lipids or nucleic acids; and circulating intimal smooth muscle cell antigens or granuloma cytokines and TWAR organisms, antigens, lipids or nucleic acids.

EXAMPLE 1

First Series of Patient Studies

Light and Electron Microscopic Studies and Immunoperoxidase Confirmation

Cases and tissue samples

This study was done on young adult men coming to autopsy 8-36 hours after death and is on hearts received for examination at the Pathology Department of the National Centre for Occupational Health in Johannesburg, South Africa, during 1989 to 1990. Most were gold miners; four were black, two white, and one Indian. No note of respiratory disease or of any animal or bird contacts was made in the limited histories available. Seven cases of coronary atheroma lesions were examined electron microscopically and by Chlamydia immunoperoxidase techniques (FIG. 1).

Lesions selected were fatty streaks and fibrolipid plaques of coronary arteries. Control tissues came from five autopsy cases whose coronary arteries were normal by gross and microscopic examination (FIG. 2).

Light microscopy

Tissues were fixed in 10% formalin and processed by standard method for light microscopy. Sections of 5µ were stained with H & E and Masson. This was used as a guide to the staging of the lesion and the pathological changes and the selection of areas to be examined.

Cases I and II were early atheroma characterized by fatty streaks. Cases III through VI were later lesions consisting of fibrolipid plaques (FIG. 3). Central lipid-rich core areas were seen in the plaques. Case VII was a complicated plaque showing degenerate, interstitial tissue and early calcification.

Electron microscopy

The thickest part of the lesion was cut across and fixed in 3% glutaraldehyde for 12 hours. Alter an overnight buffer wash the tissue was post fixed in 2% aqueous osmium tetroxide for one hour. The tissue was processed as per standard method, embedded in Spurr's epoxy resin, and sectioned for electron microscopy. The tissue was examined under a Jeol 1200 EX II electron microscope. Two sections were cut per block, and sections were examined for up to 10 hours per section until suitable areas were found and photographed.

10 cases were examined by electron microscopy. Four (cases I, II, III, and VII) showed structures similar to TWAR organisms, five (cases IV, V, VI, VIII, and IX) showed features of possible remnants or degenerate forms of these structures, i.e., vesicles of myelinoid bodies. One case showed no definite structures resembling TWAR organisms.

The structures characteristic generally of chlamydial bodies, and specifically C. pneumoniae TWAR organisms were found in all stages of the presently defined arterial chlamydial granulomatous disease. In two (cases I & II) the structures were found in early lesions in intimal smooth muscle cells adjoining a fatty streak. In seven (cases III-IX) the structures were found extracellularly in the central necrotic lipid area of the fibrolipid plaque and in surrounding macrophages; and in two (cases VII & VIII) the structures were also found in relation to early calcification.

The lipid-rich core of the fibrolipid plaque (10) appeared to be the central lesion. All seven cases examined ultrastructurally showed so-called vesicles (10) with similar features of TWAR-like organisms in the lipid-rich core of the fibrolipid plaque (FIGS. 4A and 4B).

In the adjacent intima and in early lesions similar structures were found in the intimal smooth muscle cells. These cells also showed other structures of the TWAR organism, namely reticulate and intermediate bodies. Fragmentation and rupture of these muscle cells were seen, and engulfment of fragments of the muscle cells by foam cells (macrophages) was also noted. Rupture of cells with release of these organisms into the interstitium was a common finding.

Immunoperoxidase stain

Formalin-fixed and paraffin-embedded tissues were used for immunoperoxidase staining. The immunoperoxidase staining was conducted using the avidin-biotin-peroxidase method of Hsu et al. (6) using a Vectastain ABC Kit (Vector Laboratories, Inc., Burlingame, California, U.S.A.) as previously described (7). The following murine monoclonal antibodies were used: 1 ) Chlamydia genus-specific, CF-2, against LPS; 2) C. pneumoniae species-specific, RR-402; 3) C. trachomatis species-specific, KK-12, against the major outer membrane protein; and 4)PP-13 specific against a psittacine strain PS-1 of C. psittaci (used only for staining case III). Production and specificities of these antibodies, except PP-13, have been described (8,9). The dilutions of antibodies used were predetermined to optimize for tissue staining. Normal ascetic fluid obtained from mice injected with myeloma cells was used for antibody control. HeLa cell monolayers infected with C. pneumoniae strain TW-183 and C. trachomatis strain B/TW-5/TO were included as controls each time.

Immunoperoxidase stain was positive in cases II, III, IV, V, and VI and negative in cases I and VII (FIG. 1 ). Staining was present in the cells around the plaque (all five positive cases) (FIG. 5) and often in areas with calcification (cases II and VI). Cells in the smooth muscle layer were occasionally stained (cases III, IV, V, and VI). This staining pattern correlated with the finding of TWAR-like organisms in the electron microscopy described above. Staining was widespread in cases II, III, and V and minimum in cases IV and VI. The reactions were positive against the Chlamydia genus-specific and *C. pneumoniae* species-specific monoclonal antibodies and negative against the *C. trachomatis* species-specific monoclonal antibody and normal ascetic fluid (FIG. 5). Case III was also tested with monoclonal antibody against a *C. psittaci* strain and was negative.

Coronary artery tissues from five control cases were negative (FIG. 2). One exception showed a heavy haemosiderin deposition in the subintima with a nonspecific attachment of the stain to this material. The positive and negative controls of cell monolayers infected with either *C. trachomatis* or *C. pneumoniae* reacted according to the monoclonal antibodies tested.

Discussion

The results presented in this Example show structures resembling Chlamydia TWAR organisms in the earliest lesions of atheroma. The TWAR organisms appear to injure intimal smooth muscle cells with subsequent fragmentation of these cells. Attachment of muscle cell fragments to the surface of macrophages (foam cells) was observed. The macrophages apparently take up the TWAR organisms, enlarge and rupture, liberating the multiplying organisms into the interstitium and surrounding cells. The process results in formation of a microcolony of chlamydias which, under the light microscope, appears as a central necrotic area of atheroma. At a later stage the organisms appear to degenerate forming myelinoid bodies or calcified bodies. At this time the lesion, under light microscopy, is complicated by neovascularization, fibrosis, necrosis, calcification, and lipid deposition.

Previous ultrastructural studies have illustrated structures that have been designated as vesicles, myelinoid bodies, or electron microscopic dense bodies. It is suggested that these may represent hitherto unrecognized degenerate TWAR organisms.

The structures in the electron micrographs are considered to be TWAR organisms for the following reasons: a) examination shows different recognizable stages in the chlamydial life cycle, with reticulate bodies and intermediate and elementary bodies (Chlamydia is the only known group of organisms that has this developmental cycle); and b) close examination of inclusion bodies shows pear-shaped structures with features unique to *Chlamydia pneumoniae* TWAR elementary bodies. Confirmation of arterial chlamydial infection was provided (see Example 2) by the finding of chlamydial TWAR organisms in atheromatous lesions in various arteries that were positively identified by immunocytochemistry, electron microscopic examination, polymerase chain reaction (PCR), and comparison of PCR-amplified arterial nucleic acid nucleotide sequence with the reported nucleotide sequence of *C. pneumoniae* rRNA genes. Association of the herpes virus group, e.g., herpes simplex virus and cytomegalovirus, with atherosclerosis has been demonstrated by similar immunocytochemical techniques and DNA in situ hybridization (15–17).

EXAMPLE 2

Second Series of Patient Studies

Light and Electron Microscopic Studies with Immunoperoxidase and PCR Confirmation Cases and Tissues The cases studied were 31 male and 5 female adults, autopsied 8–36 hours after death. The cases were taken mainly from the Pathology Department of the National Centre for Occupational Health and also from other autopsy centers in Johannesburg, South Africa, from May 1 to Nov. 8, 1991. There were 21 Caucasian, 9 Black, and 6 Indian or mixed race. Twenty-two cases were ages 30 or younger; the remaining cases were from 32 to 83 years of age. Causes of death for most of these cases were trauma, accident, or homicide. The other cases died from malignancy, coronary heart disease, cerebrovascular accident, renal failure, and Parkinson's disease. There was no respiratory disease or animal or bird contact indicated in the available medical records.

At the time of autopsy, coronary arteries were dissected and fixed separately in 10% buffered formalin, Carnoy's and Karnovsky's fixatives. Tissues were preserved separately in chlamydia transport medium for isolation. Post-mortem sera were also obtained; however, many of these were hemolyzed. The post-mortem blood was collected mainly from either the hepatic vein and iliac artery or occasionally the carotid artery or left ventricle. Fresh tissues and sera were frozen at −70° C. and shipped from Johannesburg to Seattle, Washington, via air freight in dry-ice packages. Fixed tissues were shipped at ambient temperature. Tissues for isolation and sera were kept in a −70° C. and −20° C. freezer, respectively, until tested.

Fifteen early lesions or fatty streaks and 21 late lesions or fibrolipid plaques of coronary arteries were studied. Of the 15 early lesions, all but one were under age 30. Control tissues were obtained from three adults and a one year-old child. Controls were selected on the basis that no atheroma was found either in the left common coronary or the left anterior descending branch by macroscopic or microscopic examination. The control tissues were obtained from these sites. In addition, normal coronary artery tissues adjacent to atheromatous lesions were obtained from two cases.

Selection of Tissue Sections

Tissues were processed according to the methods described in Example 1.

The lesions were sectioned lengthwise, if possible, otherwise transversely. The sections were take with a special object of obtaining the central main part of the lesion and not adjoining nonspecific fibrosis. Identification of chlamydial infection of arterial tissues requires that the portion of the artery to be examined first be selected for the presence of fatty streaks and/or fibrolipid plaques. Histological sections prepared from these regions of arteries must also be selected to identify sections in which lipid deposits form a central core of the lesion. Such sections are then suitable for light microscopic and transmission electron micrographic analysis. The stained sections were useful as a guide to stage the lesions of arterial chlamydial granulomatous disease, as well as to identify those regions of the diseased tissues containing the chlamydial TWAR organisms. Regions containing characteristic features of granulomatous disease (i.e., foam cells, macrophage and lymphocyte infiltration, and fibrolipid accumulations) were used as a guide for identifying sections of the tissues useful in electron microscopic identification of TWAR organisms. Best success was achieved with histological sections prepared from the thickest part of lesions, and when this area was cut laterally to expose the fibrolipid core.

Detection of C. pneumoniae in Atheromatous Plaques

Immunoperoxidase staining of tissue sections was according to the methods described in Example 1.

Frozen tissues were used for PCR. At the time of processing the frozen tissues for isolation, the tissues were thawed and divided in two pans, one for isolation (as described below) and the other for PCR. Tissues for PCR were homogenized in a DNA extraction buffer containing 10 mM Tris, pH 8.0, 100 mM EDTA, 0.5% sodium dodecyl sulfate, and 20 μl pancreatic RNAse. DNA was isolated from tissues according to Sambrook et al. (20) and resuspended in 100 μl 10 mM Tris, pH 8.0, and 1 mM EDTA. Two different sets of C. pneumoniae-specific primers which amplify distinct target sequences were used. The first set of C. pneumoniae-specific primers, HL-1 and HR-1, result in amplification of a 474 bp C. pneumoniae-specific nucleotide sequence (21). These primers do not amplify C. trachomatis or C. psittaci nucleic acid. The parameters for amplification using this set was done as described by Campbell et al. (21). The second set of C. pneumoniae-specific primers result in amplification of an 860 bp C. pneumoniae rRNA gene sequence (22). This second target was used for confirmation that the organism was C. pneumoniae. Amplification products were visualized by agarose gel electrophoresis and considered a presumptive positive if the product was the expected molecular mass. Confirmation of products was accomplished by Southern hybridization to a digoxigenin-dUTP labeled probe using either cloned DNA of the appropriate target sequence or by using a diagnostic oligonucleotide probe derived from internal sequences. DNA probes were labeled by using the Genius ™ DNA labeling and detection kit (Boehringer Mannheim Biochemicals, Indianapolis, IN), and hybrids were detected by immunochemiluminescence using Lumi-Phos 530 according to the manufacturer's directions.

To ensure that negative results were true negatives and not the result of inhibition of PCR by inhibitors present in the clinical specimen, aliquots having the same volume as the original test sample used for PCR were seeded with 25 inclusion-forming units of lysed C. pneumoniae elementary bodies. After amplification by PCR, if a product was now detected, initial negative results were considered to be a true negative. If no amplification product was observed, it was concluded that substances inhibitory to PCR were present. Subsequently, an aliquot of the clinical sample (generally 1-2 μl) which was .demonstrated to result in amplification of specimen seeded with C. pneumoniae elementary bodies was used in the PCR reaction.

To minimize contamination risks, sample preparation was done in a separate room used only for this purpose and equipped with germicidal ultraviolet lights. Amplification in the thermal cycler was done in a separate laboratory, and analysis of gel products was done in a third laboratory.

C. pneumoniae was detected in the atheromatous plaques by immunoperoxidase in 15 of 36 cases tested, and by PCR in 11 of 29 cases tested. Seven cases were not tested by PCR because the amount of tissue was enough for isolation only. With one exception, all 15 cases were immunoperoxidase positive by both the Chlamydia genus-specific antibody and the C. pneumoniae-specific antibody. The single exception was positive by the genus-specific monoclonal antibody but negative by the C. pneumoniae-specific antibody. In total, C. pneumoniae was present in 20 of the 36 cases. Correlation of the finding of organisms with the stage of atheromatous lesions showed that C. pneumoniae was detected in seven of 15 fatty streaks and in 13 of 21 fibrolipid plaques. Immunoperoxidase staining was found mainly in the cells within the plaque (FIG. 6). Cells in the smooth muscle layer of the media and in the adventitia were occasionally stained.

FIG. 6 shows immunocytochemical staining of tissue sections (original magnification ×400) of coronary artery atheromatous plaques. The atheromatous lesion was from case 7. This case was PCR positive. The typical pear-shaped C. pneumoniae elementary bodies were demonstrated in the plaque shown in FIGS. 9 and 10, below. The control artery tissue was from a one-year old child. (FIG. 6A) Chlamydia genus-specific monoclonal antibody CF-2: positive stain; (FIG. 6B) C. pneumoniae-specific monoclonal antibody RR-402: positive stain; (FIG. 6C) control antibody (normal ascetic fluid): negative stain; and (FIG. 6D) control artery tissue with monoclonal antibody CF-2: negative stain.

Of 29 cases for which both immunoperoxidase and PCR were done, six were positive by both tests, four were positive by immunoperoxidase and negative by PCR, five were positive by PCR and negative by immunoperoxidase, and 14 were negative in both tests (FIG. 7). Three of these discrepancies were from a shipment containing 10 cases of fixed tissue which was lost; therefore the reserved tissues were tested for immunoperoxidase stain.

Artery tissues from all four control specimens were negative by immunoperoxidase (FIG. 6) and PCR. Normal tissues adjacent to atheromatous lesions from two cases were also negative. However, C. pneumoniae was not detected in the lesions of these two cases. Positive and negative controls for both immunoperoxidase staining and PCR were done for each experiment and consistently reacted in the appropriate manner.

Isolation and Serology

For culturing, tissues were homogenized in chlamydia transport medium using a tissue homogenizer and inoculated onto HL cell monolayers in a flat-bottomed shell vial as previously described (24). Cultures were stained by the direct fluorescent antibody technique using a Chlamydia genus-specific monoclonal antibody CF-2 prepared in our laboratory. Two passages were done.

Serology was done by the micro-immunofluorescence technique. Formalin-fixed whole elementary bodies of C. pneumoniae strain AR-39, a pharyngeal isolate obtained in Seattle, Washington, were used as antigen to determine the presence of C. pneumoniae-specific antibodies in post-mortem sera (25). This test is C. pneumoniae-specific and no cross reaction between the chlamydial species has been shown (26).

All attempts to isolate chlamydia were negative. Serum antibody against C. pneumoniae (IgG titers equal or greater than 1:8) was demonstrated in 26 of 34 cases from whom post-mortem sera were available for testing. C. pneumoniae was detected in the plaques of five of eight antibody-negative cases. IgM antibody (1:128) was demonstrated in only one case, an 83 year-old white male, who died from cerebral infarction. His IgG titer was 1:512. This case was immunoperoxidase- and PCR-negative. He had a moderately well-formed atheroma in the coronary artery.

Sequence Analysis of PCR Amplified Nucleic Acids

To further confirm that the amplified products were *C. pneumoniae*, the amplified DNA products from selected cases were cloned into pCR-1000 using the TA Cloning™ kit (Invitrogen Corp., San Diego, Calif.) according to the manufacturer's directions and sequenced by the dideoxy-chain termination method of DNA sequencing of Sanger et al. (23). Sequence analyses were performed by the Pustell sequence analysis program (IBI) and the University of Wisconsin Genetics Computer Group programs.

Two cases were selected for further study because they were positive by immunoperoxidase staining and also positive by PCR using two different sets of *C. pneumoniae*-specific primers which amplify distinct targets. One (case 7) was antibody negative, and the other (case 13) was antibody positive.

To confirm that the product detected following PCR using the primer set which amplify *C. pneumoniae* 16s rRNA gene sequences was *C. pneumoniae*, the amplified DNA was cloned and sequenced. In a separate experiment, purified DNA from *C. pneumoniae* isolate AR-39 was amplified by the same primer set and sequenced in order to permit direct sequence comparison of the clinical products to known *C. pneumoniae* amplified products. The resulting sequence information was compared to *C. psittaci* and *C. trachomatis* rRNA gene sequences by GenBank analysis. The DNA sequences of the amplified product from the atheroma specimens were found to be identical to the *C. pneumoniae* sequence and distinct from the other chlamydial sequences (FIG. 8).

FIG. 8 compares DNA sequences of PCR amplified case 7 DNA to *C. pneumoniae* (Cpn) and *C. psittaci* (Cps) rRNA gene sequences. Case 7 and *C. pneumoniae* strain AR-39 DNA were amplified using primers for specific *C. pneummoniae* rRNA genes. A dot indicates the same nucleotide.

Electron Microscopic Observations

Tissues fixed in Karnovsky's glutaraldehyde-paraformaldehyde fixative were fixed secondarily in osmium tetroxide. Specimens were then embedded in Epon (Ernest F. Fullman, Schenectady, N.Y.), thin sectioned, stained by urany acetate and lead citrate, and viewed in a Philips CME10 transmission electron microscope.

Histology (H & E stain) of atheromas of cases 7 and 13 showed a well-developed fibrolipid lesion. Electron microscopic examination revealed typical pear-shaped *C. pneumoniae* elementary bodies in the plaque of case 7 (FIGS. 9 and 10). Organisms were found intracellularly in foam cells. Those clearly bound by the endosomal membrane were also seen. Pear-shaped structures were also seen inside the fibrolipid plaque in case 13.

FIGS. 9A and 9B are transmission electron micrographs of foam cells that contain *C. pneumoniae* organisms; wherein the following symbols apply: FC, foam cell; N, nucleus; and, arrows in the inset point to elementary bodies. Bar: 1 μm.

FIGS. 10A and 10B are transmission electron micrographs of endosomes in a foam cell that contain pear-shaped elementary bodies of *C. pneumoniae*; N, nucleus; and arrows in the inset point to elementary bodies. Bar: 0.5 μm.

Discussion

The results presented above confirm the detection of *C. pneumoniae* organisms in coronary artery atheroma plaques by three different methods: 1) electron microscopy, 2) immunoperoxidase staining with *C. pneumoniae*-specific monoclonal antibody, and 3) identification of *C. pneumoniae*-specific nucleotide sequences in the nucleic acid isolated and amplified from atherosclerotic plaques using PCR.

Not all tissues that contained *C. pneumoniae* were positive for both antigens and DNA. Reasons for the discrepancy between the two tests could be attributed to: Different areas of the same plaque, or sometimes plaque from different portions of the same artery, were used for each test. Electron microscopic findings showed patchy distribution of chlamydial organisms in atheromatous lesions. Also, several specimens contained substances inhibitory to PCR. Thus, the necessity of using smaller sample aliquots may have reduced the sensitivity of PCR detection.

Serological examination showed chronic antibody response in these cases. However, *C. pneumoniae* organisms were also detected in five of eight antibody-negative cases. We do not know how to interpret this antibody response or if the test is accurate with post-mortem sera. For example, case 7 was positive by both PCR and immunoperoxidase stain and *C. pneumoniae* elementary bodies were detected in the plaque by electron microscopy. Yet this case was antibody negative. In previous studies by the inventor of *C. pneumoniae* acute respiratory infection, isolation positive but antibody negative cases have been seen, although such cases were rare. Also, in acute infection, serum antibody tends to disappear three to five years after onset. We do not yet know how long the antibody persists in chronic infection. The inability to culture the organism from these specimens is not unexpected because: the organisms are difficult to isolate; the organisms are sensitive to temperature and improper transport or storage (27); and tissue samples were obtained many hours to days postmortem.

Several characteristics of human chlamydial infection support a causal relationship between *C. pneumoniae* and arterial granuloma. First, chlamydial infections are known to become chronic and result in intensive mononuclear cellular infiltrations and eventual tissue scarring by fibrosis (28). Second, our recent in situ hybridization studies of *C. trachomatis* in tissues of experimental monkey models, and in biopsies from patients with trachoma and tubal infertility, showed that in the chronic stage of disease, chlamydial DNA was present mainly in the deeper tissues and rarely in the epithelial cells (29). These results suggest that chlamydia may also have a tropism for other tissues beside epithelium. Third, both in vitro studies in cell culture (30,31) and in vivo studies in animal models of *C. trachomatis* pneumonitis, have reported that the organisms may also survive and multiply in macrophages (32). These studies indicate that macrophages may be a reservoir for chronic infection. Finally, it has been shown that *C. trachomatis* induces production of interleukin-1 (IL-1) by human monocytes (33). IL-1 in turn may induce production of collagenase and collagen and stimulate fibroblast and smooth muscle cell proliferation (34). Both are features of atherogenesis (35).

Why is *C. pneumoniae*, and not other chlamydias, associated with coronary atheroma? First, *C. pneumoniae* infections are widespread (3). Seroepidemiological studies of antibody prevalence have shown that from 40–60% of the adult population worldwide have antibodies against *C. pneumoniae*. The antibody is uncommon under the age of five years, increases rapidly from five to 20 years of age, and persists into old age. This antibody pattern suggests that virtually everyone is infected with *C. pneumoniae* at some time and that reinfection is common. Second, since lungs are the common site of *C. pneumoniae* infection, spread of *C. pneumoniae* organisms from lungs to vascular tissue of the heart is pathogenically plausible based on anatomy and physiology.

Coronary heart disease is a leading cause of death in Western countries. Well characterized risk factors include hypercholesterolemia, cigarette smoking, hypertension, diabetes, and family history. One of the other contributing factors that is ill-defined is infection. Among well established infectious causes of atherosclerosis are herpes viruses (15–17,37). Studies conducted by Saikku et al. in Finland based on seroprevalence of *C. pneumoniae* antibody suggest a possible correlation between chronic *C. pneumoniae* infection in both acute and chronic coronary heart disease (4). Saikku et al. have subsequently extended their studies to evaluate the relationship between "chronic" *C. pneumoniae* infection and coronary heart disease using sera from the Helsinki Heart Study, a prospective five-year investigation of dyslipemic middle-aged males (19). The results of this study suggest that *C. pneumoniae* infection is a significant risk factor for development of coronary heart disease. In the United States, a case control study by Thom et al. reported a relative risk of 2.0 between *C. pneumoniae* IgG antibody titers and angiographically diagnosed coronary artery disease (5).

The results presented above are limited to autopsy specimens from South Africa. Patients' past history and clinical and laboratory information were not available. However, there is no reason (based on the above-discussed seroepidemiological studies) that this phenomenon should exist only in persons living in South Africa, and patients in other geographical areas should exhibit similar features of the herein-described arterial chlamydial granulomatous disease.

EXAMPLE 3

Third Series of Patient Studies

General Histological Features of Arterial Chlamydial Granulomatous Disease and Proposed Etiological Mechanisms Cases The arterial tissues examined came from autopsies and cardio-pulmonary organs received at the National Centre of Occupational Health, other autopsy centers, and biopsies from operations. The cases studied were collected over a five-year period and numbered roughly 2500 from 1987–1992. The ages ranged from 19 years to about 85 years of age. The cases were predominantly male. Races included Blacks of various South African race groups, Whites, Coloreds, and Indians. Cases were derived mainly from mining areas including all parts of South Africa, the Witwatersrand and the Reef, Orange Free State, North Western Cape, Natal, Transkei, and other occupational areas. The causes of death were mainly trauma, but also included all natural causes including coronary artery disease and forms of atheroma, malignancies, infections, etc.

The general histological description of arterial chlamydial granulomatous lesions was based on examination of a large sample of patients (i.e., approximately 2500) and a selection of samples from 46 different patients. The arterial tissues examined were derived from aorta, coronary arteries, and femoral arteries and involve all stages of disease, i.e., from very early to very late. Eight patients were examined by electron microscopy alone, seven by electron microscopy and immunocytochemical stain by immunoperoxidase method, and 31 by electron microscopy, immunocytochemical stain, polymerase chain reaction, and serologically by the microimmunofluorescent test.

Histological Description

Samples were prepared according to the methods described in Examples 1 and 2. Tissue samples were generally suitable for use in electron microscopy if collected and prepared less than 36 hours postmortem.

The macroscopic features of the lesions were indistinguishable from those described in Examples 1 and 2. The histological features were dependent on two factors. First, the lesions varied with the plane of section taken. These lesions as a rule were small and patchy, and the histological features varied in different sections of the same lesions. Second, the lesions seen under the light microscope depended on the stage of the disease. The typical lesion were situated in the lower intima and consisted of a cellular reaction with central necrosis (FIGS. 12–16). The findings are summarized in Table 1, below.

TABLE 1

Summary of the Light and Electron Microscopic Findings of *Chlamydia pneumoniae* in granuloma lesions

| Technique | Early Lesions Cellular Infiltrate | Granulomatous Lesions Characteristics | Late Complicated Lesions |
|---|---|---|---|
| Histology of Selected Stained Section of Lesions; Examination of the Intima | 1. Focal necrosis of intimal smooth muscle cells above the internal elastic lamina with enlargement, fusion, rupture and fragmentation of these cells (FIG. 15); 2. Oedema in relation to the focal areas of necrosis (FIG. 15); 3. Subendothelial round cell infiltrate (FIG. 16); and, 4. Certain macrophages have taken up fat and become foam cells, others have enlarged and ruptured. | 1. Central necrotic area with surrounding cellular infiltrate containing Giemsa-positive intracytoplasmic inclusion bodies (FIGS. 12–14); 2. Gradual overlying fibrosis; 3. Early calcification in areas of necrosis. | Fibrosis Calcification Neovascularization Hemorrhage Fissuring and rupture of necrotic material with clot formation Aneurysm formation |
| Transmission Electron Microscopy | Pear-shaped elementary bodies in intimal smooth muscle cells; occasional reticulate and | TWAR organisms visible in sections in the interstitium (FIG. 20), and in necrotic | In the late healed lesions TWAR organisms are sometimes seen. |

TABLE 1-continued

Summary of the Light and Electron Microscopic Findings of
*Chlamydia pneumoniae* in granuloma lesions

| Technique | Early Lesions Cellular Infiltrate | Granulomatous Lesions Characteristics | Late Complicated Lesions |
|---|---|---|---|
| | intermediate forms of TWAR organisms (FIGS. 17–19) | areas, and in surrounding intimal smooth muscle cells and foam cells (FIG. 11) | Collagen bundles. Calcification. |

*Histological Examination of Selected Stained Section of Lesions:
a) Media: Occasional cases show focal areas of necrosis of muscle cells and oedema;
b) Adventicia: Late complicated lesions sometimes show a perivascular round cell infiltrate around the vasa-vasorum.

In summary, the cellular reaction consisted of cells with features of smooth muscle cells, macrophages, and occasionally lymphocytes. Plasma cells and polymorphonuclear leukocytes were not observed. The cells in the lesions showed various degenerative changes including enlargement, fatty change, and foam cell formation. Rupture, fragmentation, and fusion of cells with giant cell formation was also noted. Some of the cells showed typical diagnostic chlamydial cytoplasmic inclusions. The inclusions were usually diffusely distributed in the cytoplasm of the cells, and were very occasionally seen in cytoplasmic vacuoles. The cells containing these inclusions were patchy and focal in distribution and were observed mainly adjoining the central necrotic area. The inclusions were only observed with Giemsa staining and sometimes with PAS and Masson staining. The central necrotic area showed features similar to other necrotic lesions, with loss of structure and cholesterol cleft formation. Iron-positive material and early calcification was occasionally seen in this area. The only distinguishing feature which we observed in these necrotic areas was that occasionally rupture of the adjoining inclusion-body-containing cells occurred with release of organisms into the periphery of the necrotic area, and this was seen as small granules.

Figure 17:

The electron microscopic features of the lesions are characterized by the results presented in FIGS. 17–20:

FIG. 17 shows a smooth muscle cell with vacuoles ("1") containing pear-shaped bodies showing a periplasmic space and outer membrane blebs ("2"). (Original magnification 35,000×. A bar=200 nm.)

Figure 18A:
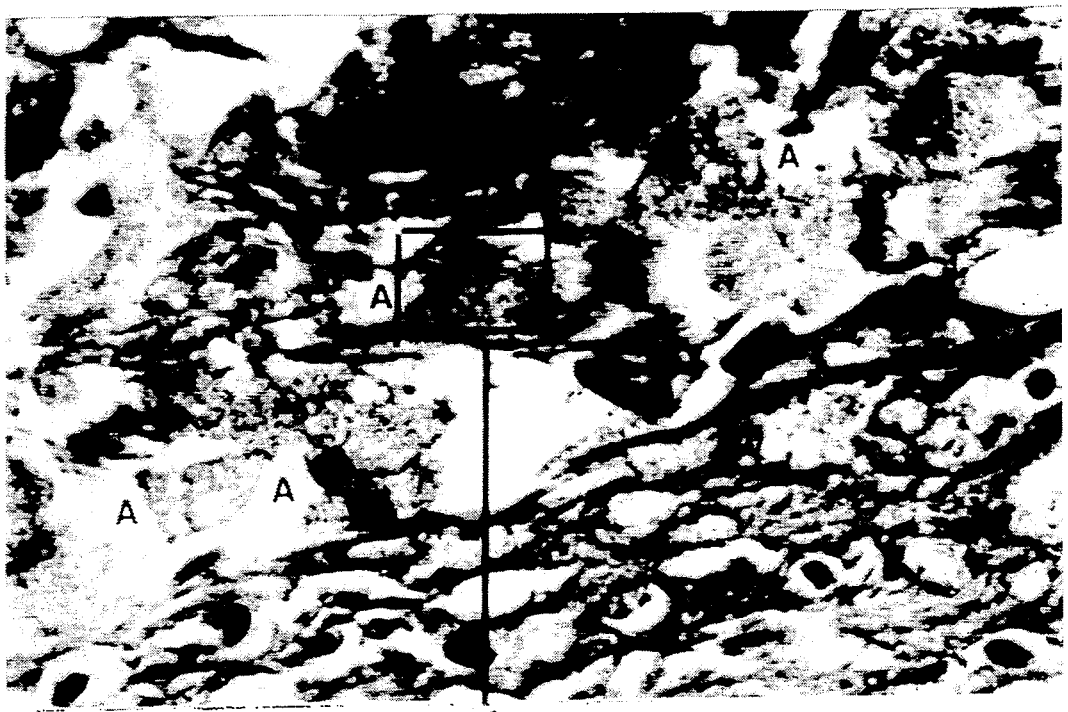
Figure 18B:

FIGS. 18A and 18B show intimal smooth muscle cells containing reticulate bodies ("1") and elementary bodies ("2"). (Magnification of FIG. 18B is 20,000×.)

Figure 19:

FIG. 19 shows fragments of intimal smooth muscle cell containing TWAR organisms.

Figure 20A:
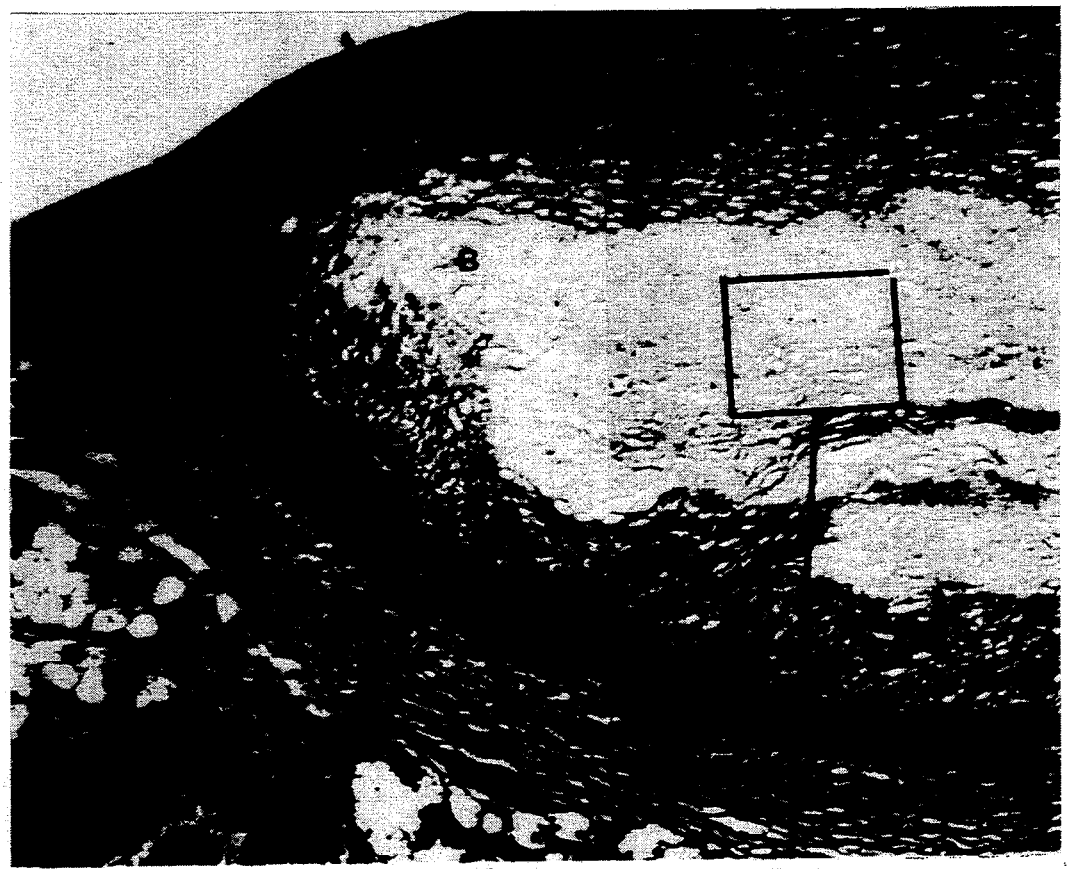
Figure 20B:
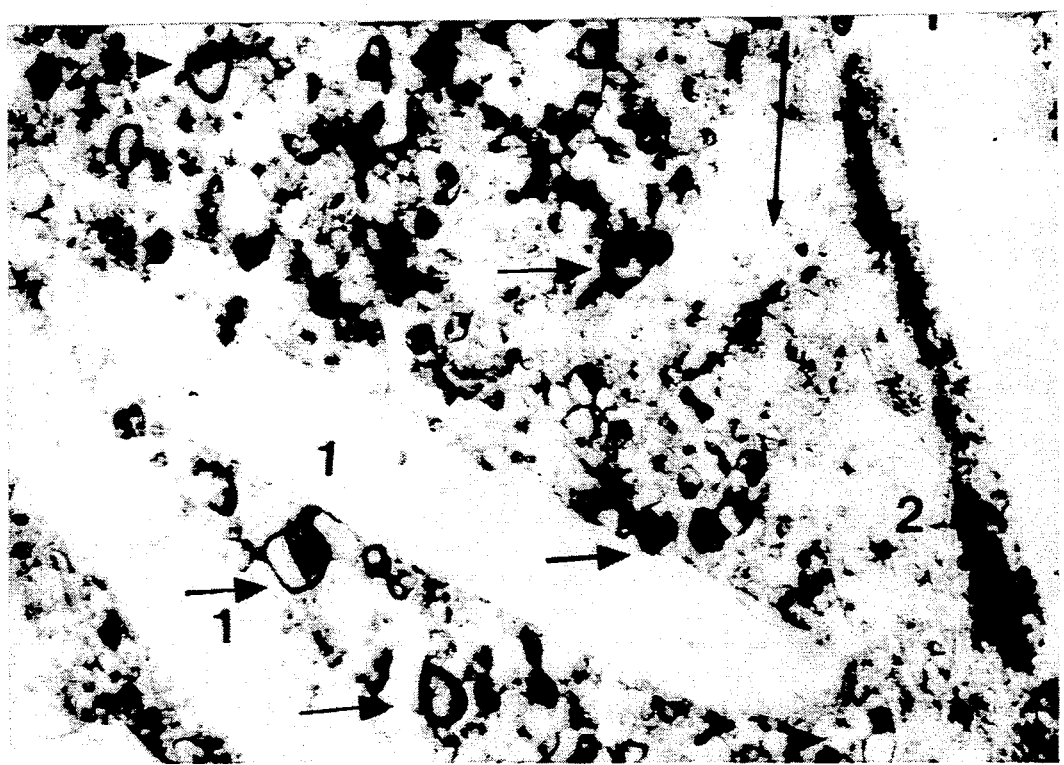

FIGS. 20A and 20B show elementary bodies (arrows) in interstitium and in relation to cholesterol ("1") and collagen bundles ("2").

Discussion

Figure 15:
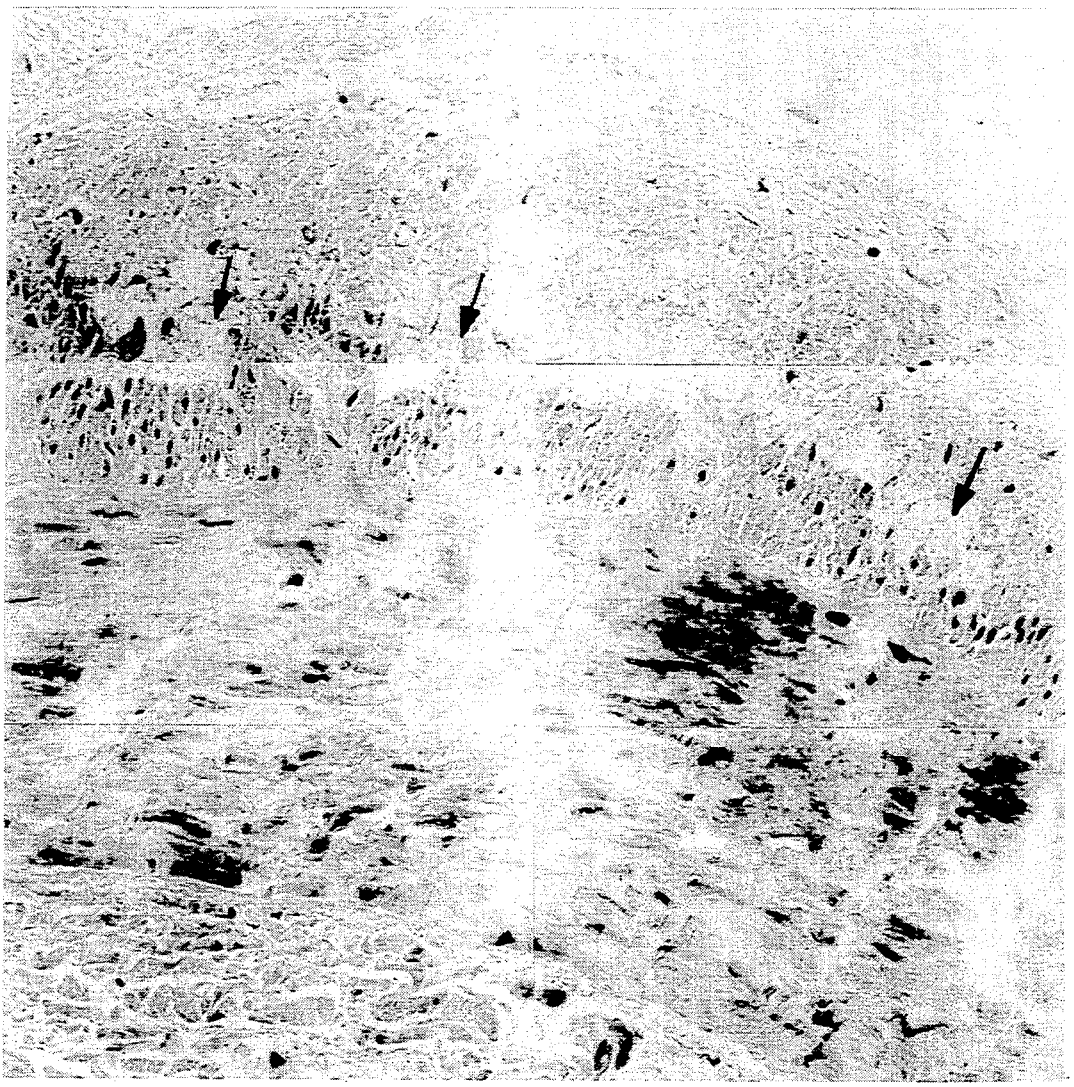
FIG. 15 shows patchy intimal smooth muscle cell necrosis with a moth-eaten appearance of the cells and also oedema (arrows).

To be termed a "granuloma" or "granulomatous lesion" a fibrotic lesion must, in general, conform to certain well-known and accepted histological criteria (see the Definitions, above). The arterial lesions described in the present Example (and in Examples 1 and 2 above) conform with accepted histological criteria identifying a granuloma. In particular, the present histological and electron microscopic findings are consistent with the following stepwise progression of disease:

(1) Initially, intimal smooth muscle cells are infected by *Chlamydia pneumoniae* TWAR organisms, and undergo rupture and fragmentation (FIGS. 15, 17, and 19).

Figure 3:
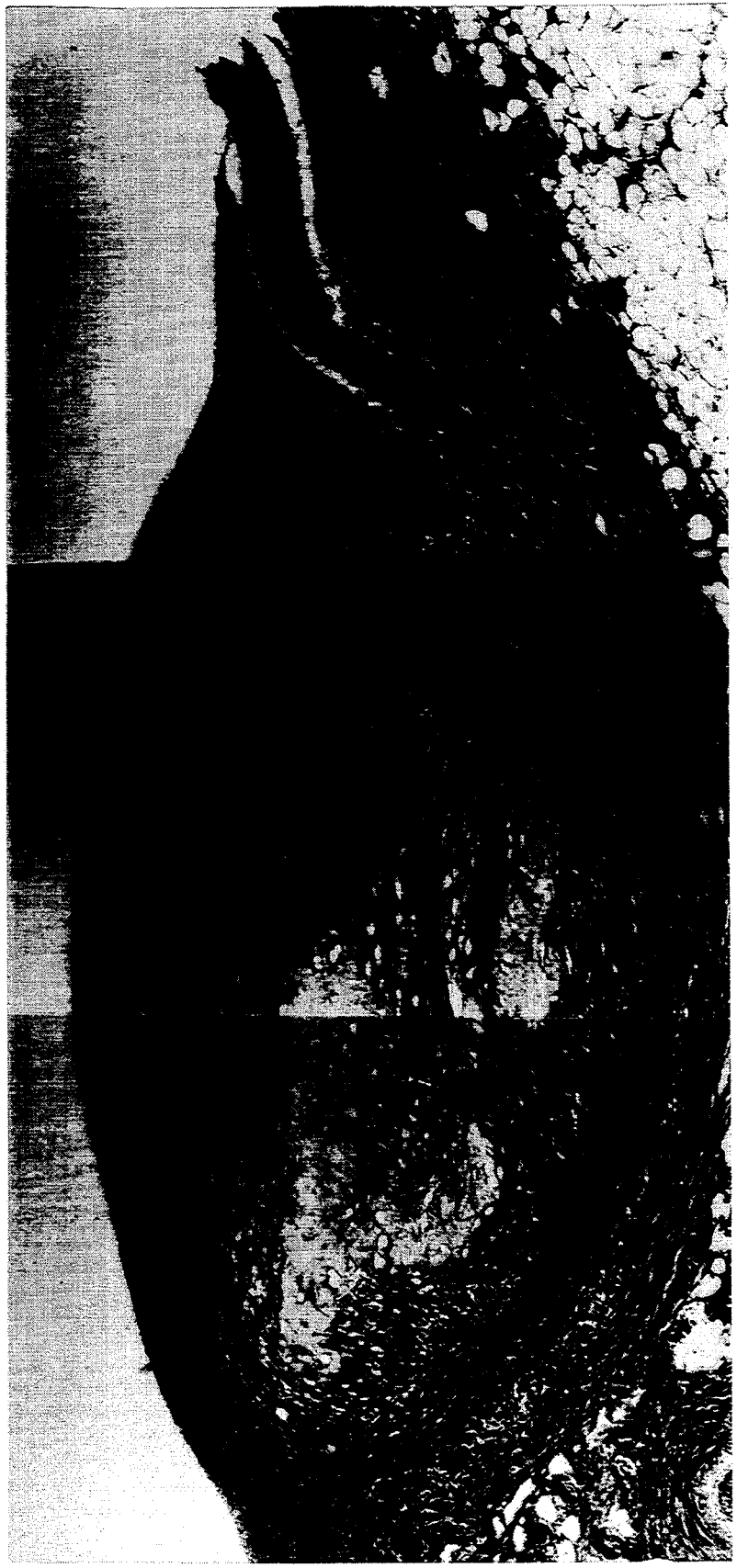
Figure 5:
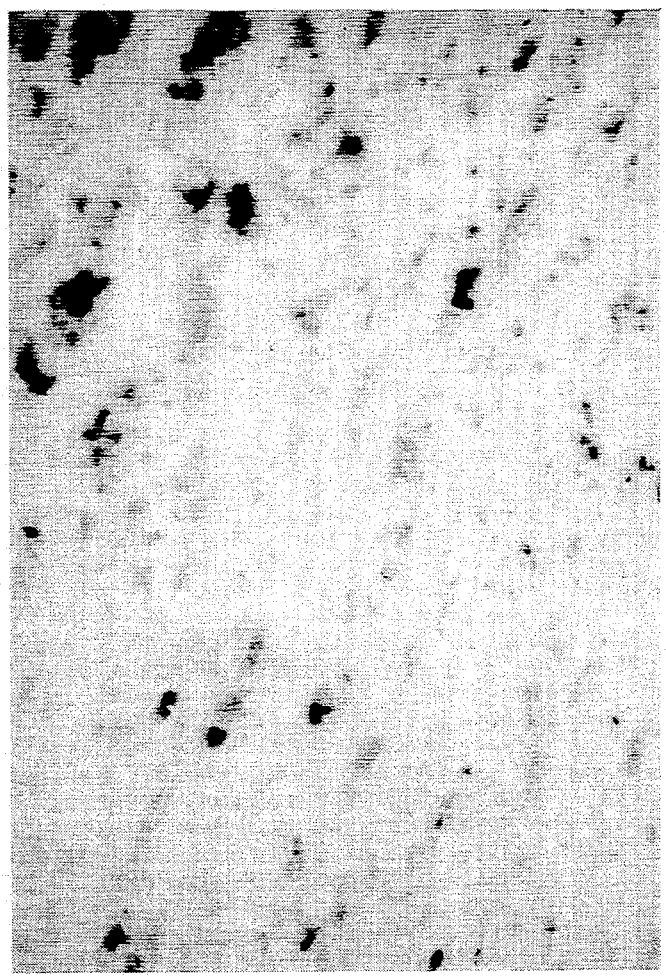
Figure 10A:
Figure 10B:
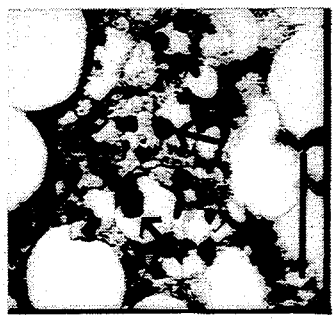
Figure 11:
FIG. 11 shows foam cells with typical *Chlamydia pneumoniae* elementary bodies.
Figure 12:
FIG. 12 shows arterial lesion with central necrosis and tissue reaction (enclosed in the square).
Figure 13:
FIG. 13 is at higher power showing granuloma cells, giant cells, and inclusion bodies of *Chlamydia pneumoniae* ("A").
Figure 14:
FIG. 14 shows granulomatous reaction and inclusion bodies ("A").
Figure 16:
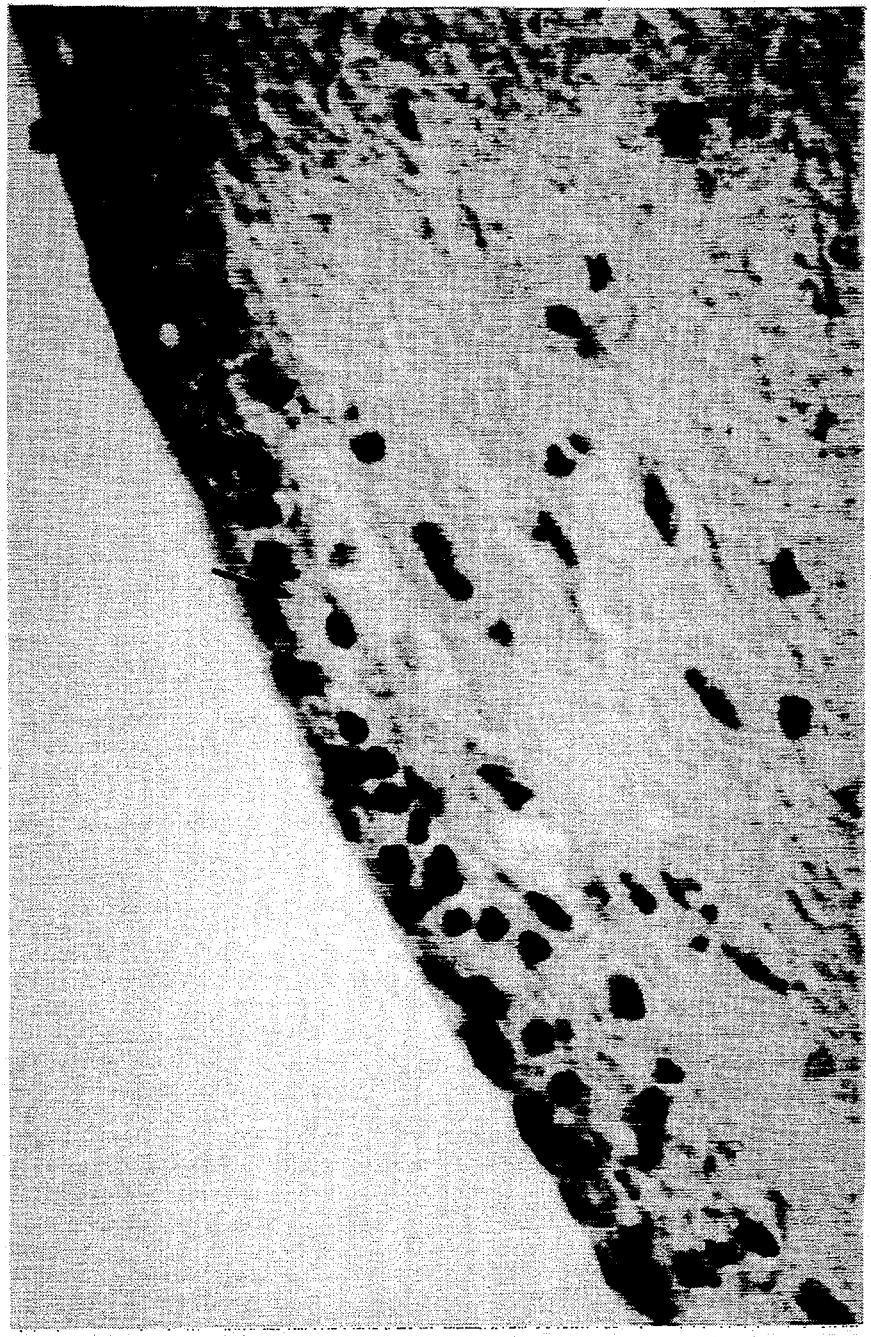
FIG. 16 shows the superficial monocyte/macrophage infiltrate in reaction to the smooth muscle cell necrosis. Note early foam cell formation (arrow).

(2) Macrophage (or blood monocyte) infiltration into the intima is triggered as an immune response to the infection. Macrophages in the site ("1") phagocytize dead and dying smooth muscle and intimal cells and TWAR organisms (FIGS. 11 and 16).

(3) A central lipid-rich necrotic core eventually develops that consists of vesicles and lipid herein shown to consist mainly of *Chlamydia pneumoniae* TWAR organisms and remnants of foam cells and degenerating smooth muscle and interstitial cells (FIG. 20).

(4) Next, smooth muscle cell proliferation occurs as a reaction to the chronic infection and to retention of chlamydial organisms in the lesion by the above-identified processes.

(5) Finally, fibrosis is a response of smooth muscle cells to the smoldering infection process, which exacerbates the luminal obstruction.

These histological findings provide a series of criteria for diagnosis and staging of *Chlamydia pneumoniae* lesions of arteries, and for assessing the extent of tissue damage caused thereby.

EXAMPLE 4

Fourth Series of Patient Samples

Detection of Arterial Chlamydial Granulomatous Disease in Coronary Bypass Grafts Cases Studied Twenty-five postmortem cases were studied in which coronary bypass surgery was conducted from a few months to five years earlier. The cases were all men over 50 years of age. The cause of death was sometimes unrelated to the bypass operation or coronary artery disease. The donor graft was from a vein of the lower leg and free from atheroma.

Standard histopathological and electron microscopic methods for identifying *C. pneumoniae* were utilized as described in Examples 1 and 2.

Results

Among the changes observed were transformation of the femoral vein graft to develop characteristics of arterial tissues and areas of necrosis and fibrosis in the intima that were macroscopically indistinguishable from atheroma. The histological lesions were similar to the granulomatous and necrotic lesions described in other arteries, as discussed in Examples 1 and 2.

The extent of the lesion varied in relation to the period of time which had elapsed between the bypass operation and the examination of the postmortem tissue samples, i.e., more severe lesions were frequently observed in cases where more time had elapsed. The smooth muscle cell proliferation we observed in these histological sections is believed to account for the pattern of arterial chlamydial granulomatous disease, as summarized below in Table 2.

TABLE 2

| Legion Stage | Histological Features of Coronary Bypass Grafts | | | |
|---|---|---|---|---|
| | Granuloma | Necrosis | Fibrosis/ Calcification | Smooth Muscle Cell Proliferation* |
| Early | | | | |
| Stage I | +/− | +/− | — | — |
| Stage II | present | present | early | occasional |
| Late | | | | |
| Stage III | present | present | present | present |
| Normal Control: | — | — | — | — |

*Adjacent to the diseased area of tissue.

Discussion

The data presented above suggests that venous graft develops the same arterial granulomata found in the adjacent diseased arteries which they are bypassing, namely, fibrosis, calcification, and progressive formation of lesions. The results presented in Examples 1 and 2, combined with those described here, suggest the spread of chlamydial infection from sites of disease in coronary arteries into grafted femoral venous tissues.

Patients with obstruction of Coronary arteries should, prior to bypass surgery, be evaluated to determine whether the diseased arterial tissues are infected with chlamydia. If this is found to be the case, therapeutic intervention is indicated to control (e.g., with antibiotic therapy) the spread of infection from the primary site in the diseased coronary artery into the femoral venous graft.

Similar principles of treatment apply to treatment of post-coronary bypass arterial chlamydial granulomatous diseases, as apply to those described for treatment of atheromatous lesions; see Examples 7–8.

EXAMPLE 5

Fifth Series of Patient Samples

Detection of Arterial Chlamydial Granulomatous Disease in Restenotic Lesions

Cases Studied

Cases of arterial chlamydial granulomatous disease discussed in this Example involved patients subjected to surgical catheterization procedures involving dilatation (e.g., by balloon catheter) and stripping to remove luminal obstructions (e.g., by retracting the inflated balloon catheter from the vessel). The cases under study also included rotor-brator specimens taken from coronary arteries during catherization procedures.

Tissue samples are examined following the methods and instructions provided in Examples 1 and 2, namely, 1)histochemical methods (e.g., with H&E-stained sections), 2)transmission electron microscopy; 3)immunocytochemical staining for *Chlamydia pneumoniae*, and/or 4) detection of *Chlamydia pneumoniae* nucleic acid by polymerase chain reaction.

Results

The histological features of the balloon dilatation cases of coronary arteries routinely showed various changes among which are included hemorrhage and formation of the plaque deposits in the tissues adjoining the arterial intima. Histological examination also revealed fissuring of overlying fibrous tissue and leakage of necrotic material (that may include chlamydial TWAR organisms) into the lumen, and signs characteristic of tissue wound healing of these latter areas.

In such catheterization procedures for removing luminal obstructions, there was tearing of the tissue with spreading of the necrotic and granulomatous material, and subsequent healing of the torn tissues accompanied by smooth muscle cell proliferation. Catheterization procedures may therefore spread any resident chlamydial infection (i.e., such as described in Examples 1–3) so that new lesions result in previously healthy intimal layers of the artery.

Such restenotic lesions in certain patients contain chlamydia which can be identified by the methods described herein. TWAR organisms can be identified in restenotic lesions (e.g., following angioplasty) by histology techniques, immunocytochemical staining, polymerase chain reaction, and/or diagnostic imaging techniques (described below in Example 6).

Discussion

Restenosis occurring in arterial tissues following angioplasty has been thought to result from smooth muscle cell proliferation occurring as a result of wounding and growth factor release in certain patients. The results herein suggest a progressive arterial disease that is spread by the surgical catheterization procedures designed to remove lumenal obstructions. Histological studies conducted herein suggest continuation and progression of the chronic chlamydial infection and granulomatous processes in angioplasty sites, with possible dissemination of the TWAR organism to sites of previously healthy tissue. For this course of infection, similar principles of treatment (to those described above) may be expected to yield a beneficial result in the treatment of restenosis following angioplasty.

EXAMPLE 6

Detection of Arterial Chlamydial Granulomatous Disease in Patients by Diagnostic Imaging Diagnosis of arterial lumen narrowing attributable to Chlamydia infection It is routine in the art to image portions of arteries where lumen narrowing is restricting blood flow. For example, angiography and ultrasonic imaging techniques are routinely used for this purpose. Those skilled in the art will also recognize that diagnostic imaging, e.g., of tumor antigens, may be accomplished using a catheter to deliver the imaging agent close to the antigen site.

The present diagnostic procedure for identifying arterial chlamydial infection sites of restricted arterial blood flow relies on coincidence in signal showing both narrowing of the lumen and the presence of chlamydial antigens at the same location. The procedure is useful for identifying chlamydial infection in coronary artery, carotid artery, or femoral artery, where lumen narrowing is determined by angiography or ultrasonography.

Procedure

Catheter procedures designed for angiography are also suitable for delivery of both an X-ray opaque contrast agent and a diagnostic Chlamydia-specific imaging agent. Briefly, the catheter is threaded into the artery and placed upstream of the blockage, and the contrast agent and radiolabeled monoclonal antibody are either delivered together, or one after the other. After a suitable time the luminal narrowing is detected by X-ray techniques, and the presence of the radiolabeled imaging agent is detected at the same site using a gamma camera, or, with certain imaging agents (i.e., $^{131}$I) in certain locations (i.e., in carotid arteries), using a sensitive hand-held Geiger-Muller counter.

Results

The radiolabeled antibody binds to *Chlamydia pneumoniae* organisms in or associated with the smooth muscle cells, macrophages, or interstitium in the granulomatous lesions in the artery. The uptake of radioactivity is revealed by radionuclide imaging. If the lesions are due to *Chlamydia pneumoniae*, the location of radioactivity should be at the location of the arterial narrowing revealed by angiography or ultrasonography.

Discussion

Microscopic observations reveal that *Chlamydia pneumoniae* TWAR organisms are present in the smooth muscle cells and macrophages, and interstitially in the necrotic tissues at all stages of arterial chlamydial granulomatous disease. The presence of chlamydial antigens in regions of luminal narrowing is diagnostic for *Chlamydia pneumoniae* arterial disease and can be used to measure the course of the disease and the extent of the lesions. Representative materials and methods are discussed below.

Specific Binding Partners

Chlamydia genus-specific polyclonal and monoclonal antibodies, i.e., CF-2, or *Chlamydia pneumoniae* TWAR-specific monoclonal antibodies like RR-402 or TT-205, may be used to detect TWAR organisms. Effective imaging agents may also include use of IgG, IgM, IgG, IgA, and the like, and antibody fragments such as F(ab')$_2$, Fab', Fab, Fv, sFv, or complementary determining regions (CDR) regions of antibodies recombinantly derived in a variety of fusion proteins.

Other specific binding partners that may be useful include natural and recombinant proteins that bind to chlamydial antigens, e.g., mammalian cell surface receptors for Chlamydia and lectins.

Label

A wide variety of methods are available to prepare *Chlamydia pneumoniae*-specific monoclonal antibodies suitable for use in diagnostic imaging procedures. $^{99m}$Tc is considered a suitable label for diagnostic imaging in this protocol.

Linker

Many conventional linker methodologies may be useful for conjugating the label to the specific binding partner, including covalent conjugation through DPTA (diethylene-triaminepentaacetic acid), BATO (boronic acid adduct of technetium dioximes), and direct addition to reduced or thiolated specific binding partner.

EXAMPLE 7

Prophylactic Treatment of Arterial Chlamydial Granulomatous Disease

Patients who may benefit from treatment for arterial chlamydial granulomatous diseases are recognizable to the .practitioner by their falling into the following categories.

Patient categories

I. Seropositive patients

Seropositive is defined as presence of antibodies against *Chlamydia pneumoniae.* Patients in this category are either:

A. Patients with a current arterial chlamydial infection: Current infection is defined as a seroconversion, a four-fold rise or drop in antibody tiler in either IgM or IgG serum fraction, a titer of greater than 1:16 in the IgM serum fraction, or equal or greater than 1:512 in the IgG serum fraction; or, B. Patients with a past chlamydial infection: Past infection is defined as IgG antibodies of 1:8 to 1:256.

II. Seronegative patient

Antibody negative against *Chlamydia pneumoniae.* Patients in this category either have:

A. No infection; or

B. Past infection but antibody has eclipsed (or they may be nonresponsive to the chlamydial antigen used in the antibody test).

Prophylaxis for arterial surgery

For patient category I

Category IA

Before surgery

A full course of antichlamydial chemotherapy, for example: tetracycline 500 mg qid for 14 days; doxycycline 100 mg bid for 14 days; or erythromycin qid for 14 days or 250 mg for 21 days. Other newer drugs, i.e., azithromycin, quinolone analogs, can also be used for treatment.

After surgery

Prophylactic treatment for restenosis, for example: Azithromycin 500 mg once a week for 3 to 6 months.

Category IB

Prophylactic treatment for restenosis after surgery, as in category IA.

Categories IIA and B

In high risk groups, prophylactic antichlamydial treatment for restenosis is recommended, as in category IA.

EXAMPLE 8

Treatment of Arterial Chlamydial Granulomatous Disease

Patient selection procedure

Patient selection that will benefit from the therapy.

A. Decreased blood supply

Patients with symptoms of decreased blood supply to an organ, i.e., heart, leg, and brain, with resulting symptoms of angina, claudication, and cerebral ischemia like chest pain, shortness of breath, pain in the calf on exertion, gangrene, fainting, dizziness, and other cerebral symptoms, etc.

B. Presence of antibodies suggestive of *Chlamydial pneumoniae* infection.
C. Angiographically and ultrasound-diagnosed arterial lesions.
D. Positive imaging; see Example 6.
E. Positive imaging at the same site of narrowing of arterial lumen as detected by angiography and ultrasound procedure; see Example 6.
F. Cases that have been confirmed to be *Chlamydia pneumoniae* lesions by biopsy and tested positive by histology, transmission electron microscopy, immunocytochemistry, and/or polymerase chain reaction.

Therapy

A. Acute obstruction

Surgical removal of obstruction followed by medication against *Chlamydia pneumoniae* arterial disease.

B. Nonacute obstruction

Medication against *Chlamydia pneumoniae* arterial disease.

C. Patients with no sign of obstruction

Medication against *Chlamydia pneumoniae* is recommended to prevent progression of lesions.

General principles of treatment

Prior to the present discovery of the pathogenic mechanisms involved in atheroma this disease has been accepted as being fat-related and most of the treatment was directed at lowering serum fat. Pursuant to the present disclosure, the following new general principles of treatment are recommended.

Initial Therapy
1. Drugs to prevent entry of organisms into smooth muscle cells.
2. Drugs to kill organisms in intimal smooth muscle cells.
3. Drugs to prevent necrosis of cells and release of organisms.

Secondary Therapy
4. Prevent entry of macrophages into intima by removing stimuli, i.e., organisms and cell fragments.
5. Prevent uptake of organisms into macrophages.
6. Kill organisms in macrophages.
7. Prevent release of organisms from macrophages into the interstitium.
8. The central necrotic core which consists of vesicles and fat can be decreased by:
   a) drugs which will kill organisms (i.e., vesicles) and will decrease mass of lesion;
   b) drugs against organism will kill organisms and prevent the fat formation portion derived from the organism;
   c) blocking macrophages from producing substances, i.e., tissue necrosis factor, which cause necrosis of cells and also add to the fat content.

Late lesions:
Remove stimulus, i.e., low grade smoldering chronic infection, which causes intimal smooth muscle cell proliferation and fibrosis. The organisms appear to be a nidus of calcification. Therefore, removing organisms prevents calcification of the lesions.

Medication methods

A. Routes of administration
1. Parenteral route

For acute cases the following methods of administration may be more effective:

a) give agents into the angioplasty site through catheter;
b) intravenous drip to maintain high concentration. For examples, the effective concentrations of drug to kill *Chlamydia pneumoniae* in tissue fluid (i.e., a "tissue effective dose") are:

| Drug | Minimal bactericidal concentration (microgram per ml) |
|---|---|
| tetracycline | 0.05–0.1 |
| erythromycin | 0.01–0.05 |
| clarithromycin | 0.05–2.0 |
| azithromycin | 0.125–0.5 |
| ofloxacin | 1.0–2.0 |
| sparfloxacin | 1.0 |
| temafloxacin | 20–40 |

2. Oral route: see Example 4 for treatment regimens.

B. List of drugs used

Any drugs found to be effective against the steps listed in III under general principles of treatment; also see references 39 and 40.

Discussion

The diseases of the arterial intima have been generally confined to atherosclerosis. Treatment has been exclusively focused on lipid-lowering agents because the lesion has been considered to be lipid related. In contrast, the presently disclosed therapeutic protocols focus on eliminating the chlamydial infection, i.e., the part of the lipid structures in the lesion that have previously been misdiagnosed (Chlamydia contain 30% lipid)..

The anti-chlamydial therapy which we recommend is a novel way of rapidly decreasing the fat and mass of arterial lesions caused by arterial chlamydial infections. The other generalized risk factors such as smoking, diabetes, hypertension could play a part in the risk factors of this disease, and we recommend treatment thereof. Aspirin has been shown to have an anti-inflammatory effect and may therefore play a part in the treatment. Anticoagulative treatment we believe follows rupture of the granuloma with hemorrhage .and clotting; therefore, treatment of the clot may be of value in these cases. The new method of treatment which we recommend in view of our recent findings offers a cure of the disease instead of at best with old methods of treatment a delay in the sequence of events.

Citations

1. Grayston, JT, Kuo CC, Campbell LA, Wang SP. *Chlamydia pneumoniae* sp. nov for Chlamydia sp. strain TWAR. Int J Syst Bacteriol 1989; 39: 88–90.
2. Chi Ey, XUO CC, Grayston Ti. Unique ultrastructure in Elementary Body of Chlamydia sp. strain TWAR. Int J. Syst Bacterial. 1989; 39: 88–90.
3. Grayston TJ, Campbell LA, Kuo CC, Mordhorst CH, Saikku P Thom DM, Wang SP. A New Respiratory Tract Pathogen. *Chlamydia pneumoniae* Strain TWAR. J. Infect. Dis. 1990; 161: 618–625.
4. Saikku P, Mattila K, Nieminen MS, Huttunen JK, Leinonen M, Ekman MR, Mäkelä PH, Valtonen V. Serological evidence of an association of a novel Chlamydia, TWAR with chronic Coronary Heart Disease and Acute Myocardial Infarction. Lancet, 1988; 2: 983–985.
5. Thom DH, Wang SP, Grayston JT, Siscovick DS, Steward DK, Kronmal RA, Weiss NS. *Chlamydia*

*pneumoniae* strain TWAR antibody and angiographically demonstrated coronary artery disease. Arteriosclerosis and Thrombosis 1991; 11:547-551.

6. Hsu SM, Raine L, Franger H. A comparative study of the peroxidase-antiperoxidase method and an avidin-biotin complex method for studying polypeptide hormones with radioimmunoassay antibodies. Am J. Clin Pathol 1981; 75: 734-738.

7. Patton DL, Halbert SA, Kuo CC, Wang SP, Holmes KK. Host response to primary *Chlamydia trachomatis* infection of the fallopian tube in pig-tailed monkeys. Fertil Steril 1983; 40: 829-840.

8. Kuo CC, Chen HH, Wang SP, Grayston T. Identification of New Group of *Chlamydia psittaci* Strains called TWAR. J. Clin. Microbiol., 1986; 24: 1034-1037.

9. Swanson AF, Kuo CC. Evidence that the major outer membrane protein of *Chlamydia trachomatis* is glycosylated. Infect Immun 1991; 59:2120-2125.

10. Guyton JR, Klemp KF. The lipid Rich Core Region of Human Atherosclerotic Fibrous Plaques. Am. T. Pathol., 1989; 134: 705-717.

11. Sutton GC, Demakis JA, Anderson TO, Morrissey RA. Serologic evidence of a sporadic outbreak in Illinois of infection by Chlamydia (psittacosis-LGV agent) in patients with primary myocardial disease and respiratory disease. Am Heart J 1971; 81: 597-607.

12. Grayston TT, Mordhorst CH, Wang SP. Childhood myocarditis associated with *Chlamydia tracomatis* infection. JAMA 1981; 246: 2823-2823-2827.

13. Jones RB, Priest JB, Kuo CC. Subacute chlamydia endocarditis. JAMA 1982; 247: 655-658.

14. Marrie TJ, Harczy M, Mann OE, Landymore RW, Raza A, Wang SP, Grayston JT. Culture-negative endocarditis probably due to *Chlamydia pneumoniae*. J Infect Dis 1990; 161: 127-129.

15. Benditt EA, Barrett T, McDougall JK. Viruses in the etiology of atherosclerosis Proc. Natl. Acad. Sci. USA. 1983; 80: 6386-6389.

16. Melnick JL, Petrie BL, Dreeman GR, Burek J, McCollum CH, Debakey ME. Cytomegalovirus antigen within human arterial smooth muscle cells. Lancet 1983; 2: 644-647.

17. Yamashiroya HM., Ghosh L, Yang R, Robertson AL. Herpesviridae in the coronary arteries and aorta of Young Trauma Victims. Am. J. Pathol. 1988; 130: 71-79.

18. Moulder JW, Hatch TP, Kuo CC, Schachter J, Storz J. Chlamydia Jones, Rake and Stearns 1945,55. In: Krieg NR, Holt JG, eds. Bergey's manual of systematic bacteriology, vol. 1. Baltimore: The Williams & Wilkins Co., 1984;729-735.

19. Saikku P, Leinonen M, Tenkaneo L, Linnanmaki E, Ekman MR, Manninen V, Manttari M, Frick MH, Huttunen JK, Chronic *Chlamydia pneumoniae* infection as a risk factor for coronary heart disease in the Helsinki Heart Study. Ann Int Med 1992;116:273-278.

20. Sambrook J, Fritsch EF, Maniatis T, Molecular cloning: a laboratory manual. Cold Spring Harbor Laboratory Press. Cold Spring, N.Y.

21. Campbell LA, Perez-Melgosa M, Hamilton DJ, Kuo CC, Grayston JT, Detection of *Chlamydia pneumoniae* by polymerase chain reaction. J Clin Microbiol 1992;30:434-439.

22. Black CM, Fields PI, Messner TO, Berdal BP, Detection *Chlamydia pneumoniae* in clinical specimens by species specific PCR. (submitted).

23. Sanger F, Nicklen S, Coulson AR, DNA sequencing with chain-terminating inhibitors. Proc Natl. Acad. Sci. USA 1977;74:5463-5467.

24. Kuo CC, Grayston JT, A sensitive cell line, HL cells, for isolation and propagation of *Chlamydia pneumoniae* strain TWAR. J Infect Dis 1990;162:755-758.

25. Wang SP, Grayston JT, Serologic relationship between genital TRIC, lymphogranuloma venereum, and related organisms in a new microtiter indirect immunofluorescence test. Am J Ophthalmol 1970;70:367-374.

26. Wang SP, Grayston JT, Microimmunofluorescence serological studies with the TWAR organism. In: Oriel JD, Ridway G, Schachter J, Taylor-Robinson, Ward M, eds. Chlamydial Infections. Cambridge, England: Cambridge University Press, 1986;329-332.

27. Kuo CC, Grayston JT, Factors affecting viability and growth in HeLa 229 cells of Chlamydia sp. strain TWA J Clin Microbiol 1988;26:812-815.

28. Kuo CC, Host response, In: Barron AL, ed. Microbiology of Chlamydia. Boca Raton, Fla.: CRC Press, Inc., 1988;193-208.

29. Cappucio, AL, Patton DL, Kuo CC, Moore DE, Cosgrove PA Campbell LA, Detection of *Chlamydia trachomatis* DNA genital and ocular tissues by in situ hybridization: Implication for pathogenesis. J Infect Dis 1992 (submitted).

30. Kuo CC, Cultures of *Chlamydia trachomatis* in mouse peritoneal macrophages: Factors affecting organism growth. Infect Immun 1978;h2O:439-445.

31. Yong, EC, Chi EY, Kuo CC, Differential antimicrobial activity of human mononuclear phagocytes against the human biovars of *Chlamydia trachomatis*. J Immunol 1987;139: 1297-1302.

32. Chen WJ, Kuo CC, A mouse model of pneumonia induced by *Chlamydia trachomatis*: Morphologic, microbiologic and immunologic studies. Am J Pathol 1980;100:365-377.

33. Rothermel CD, Schachter J, Lavrich P, Lipsitz EC, Francus T, *Chlamydia trachomatis*-induced production interleukin-1 by human monocytes. Infect Immun 1989;57:2705-2711.

34. Dinarello CA, Interleukin-1 and its biologically related cytokines. In: Cohen S, ed. Lymphokines and the immune response. Boca Raton, Fla., CRC Press, Inc., 1990;145-179.

35. Fuster, V, Badimon L, Badimon JJ, Chesebro, Mechanisms of disease: The pathogenesis of coronary artery disease and the acute coronary syndromes (first of two parts). N Engl J Med 1922;326:242-250.

36. Report of the Working Group of Arteriosclerosis of the National Heart, Lung, and Blood Institute. vol. 2. Washington, D.C.: Government Printing Office, 1981. DHEW Publication no.(NIH)82-2035.

37. Benditt EP, Barrett T, McDougall JK, Virus in the etiology of atherosclerosis. Proc Natl. Acad. Sci. USA 1983;80:6386-6389.

38. Kuo CC, Grayston, in vitro drug susceptibility of Chlamydia sp. strain TWAR. Antimicrob Agents Chemother 1988;32:257-258.

39. Lipsky BA, Tack KJ, Wang SP, Kuo CC, Grayston JT, Ofloxacin treatment of a *Chlamydia pneumoniae* (strain TWAR) lower respiratory tract infections. Am J Med 1990;89:722-724.

40. Grayston, T. J., Kuo, C. C., Wang, S. P., Altman, J. A new *Chlamydia psittaci* strain TWAR isolated in acute respiratory tract infections. New. Engl. J. Med. 1986; 315: 161–167.
41. Kleemola, M., Saikku, P., Visakorpi, R., Wang, S. P. Epidemics of pneumonia caused by TWAR, A new Chlamydia organism, in military trainees in Finland. J. Infect. Dis. 1988; 157: 230–236.
42. Szebeni, J., Wahl, S.M., Betageri, G. V., Wahl, L.M., Gartner, S., Popovic, M., Parker, R. J., Black, C. D., and Weinstein, J. N. Inhibition of HIV-1 in monocyte/macrophage cultures by 2',3'-dideoxycytidine5'-triphosphate, free and in liposomes. AIDS Res. Hum. Retroviruses 1990; 6:691–702.
43. Campbell, L. A., Kuo, C. C., Thissen, R. W. and Grayston, J. T. Isolation of a gene encoding a Chlamydia sp. strain TWAR protein that is recognized during infection in humans. Infect. Immun. 1989; 57:71–75.
44. Ladany, S., Black, C. M., Farshy, C. E., Osewaarde, J. M. and Barnes, R. C. Enzyme immunoassay to determine exposure to *Chlamydia pneumoniae* (Strain TWAR). J. Clin. Microbiol. 1989; 27: 2778–2783.
45. Fu, Y., Baumann, M., Kosma, P., Brade, L. and Brade, H. A synthetic glycoconjugate representing the genus-specific epitope of Chlamydial lipopolysaccharide exhibits the same specificity as its natural counterpart. Infect. Immun. 1992; 60: 1314–1321.
46. Stuart, E. S., Wyrick, P. B., Choong, J., Stoler, S. B., MacDonald, A. B. Examination of chlamydial glycolipid with monoclonal antibodies: cellular distribution and epitope binding. Immunol. 1991; 74: 740–747.
47. Karimi, S. T., Schloemer, R. H. and Wilde, C. E. Accumulation of Chlamydial lipopolyscaccharide antigen in the plasma membranes of infected cells. Infect. Immun. 1989; 57: 1780–1785.
48. Brade, L., Hoist, O., Kosma, P., Zhang, Y-X., Paulsen, H., Krausse, R., and Brade, H. Characterization of murine monoclonal and murine, rabbit, and human polyclonal antibodies against Chlamydial lipopolysaccharide. Infect. Immun. 1990; 58: 205–213.

---

The embodiments of the invention in which an exclusive property or privilege is claimed are defined as follows:

1. A method of screening for arterial chlamydial granuloma by detecting in a biological sample both a first marker associated with *Chlamydia pneumoniae* and a second marker associated with arterial granuloma.

2. The screening method of claim 1, wherein the first marker is a *Chlamydia pneumoniae* organism detected by electron microscopy, or the first marker is a *Chlamydia pneumoniae* antigen detected by immunohistochemical staining or immunoassay with a *C. pneumoniae*-specific binding partner, or the first marker is a *C. pneumoniae*-specific nucleotide sequence detected by nucleic acid hybridization with a *C. pneumoniae*-specific probe, or the first marker is a *C. pneumoniae* lipid detected by HPLC.

3. The screening method of claim 1, wherein the second marker is selected from among macrophage foam cells, fibrolipid deposits, and intimal smooth muscle cell necrosis detected by electron microscopy, or the second marker is an intimal smooth muscle-specific antigen detected by immunoassay, or the second marker is a granuloma-associated marker detected by immunoassay.

* * * * *

UNITED STATES PATENT AND TRADEMARK OFFICE
CERTIFICATE OF CORRECTION

PATENT NO. : 5,424,187  
DATED : June 13, 1995  
INVENTOR(S) : A. Shor et al.

Page 1 of 3

It is certified that error appears in the above-indentified patent and that said Letters Patent is hereby corrected as shown below:

On the title page item [56],

"Grayston,J. T." should read --Grayston, J.T--

"genu-s-specific" should read --genus-specific--

"Accumulation of infected cells." should read --Accumulation of Chlamydial lipopolysaccharide antigen in the plasma membranes of infected cells.--

| Column | Line | |
|---|---|---|
| 1 | 11 | "BACKGORUND" should read --Background-- |
| 4 | 47 | "organisms.(N=" should read --organisms. (N=-- |
| 5 | 25 | "FIG." should read --FIGURES-- |
| 6 | 5 | "(2)circulating" should read --(2) circulating-- |
| 6 | 6 | "(3)circulating" should read --(3) circulating-- |

UNITED STATES PATENT AND TRADEMARK OFFICE
CERTIFICATE OF CORRECTION

PATENT NO. : 5,424,187
DATED : June 13, 1995
INVENTOR(S) : A. Shor et al.

It is certified that error appears in the above-indentified patent and that said Letters Patent is hereby corrected as shown below:

| COLUMN | LINE | |
|---|---|---|
| 6 | 14 | "(1)hybridization" should read --(1) hybridization-- |
| 6 | 16 | "(2)amplification" should read --(2) amplification-- |
| 14 | 3 | "Alter" should read --After-- |
| 17 | 12 | "pans, should read --parts,-- |
| 20 | 63 | "*pneumoniae ."* should read --*pneumoniae,*-- |
| 25 | 23 | "*Agjacent" should read --*Adjacent-- |
| 25 | 63 | "1)histochemical" should read --1) histochemical-- |
| 25 | 64 | "2)transmission" should read --2) transmission-- |

UNITED STATES PATENT AND TRADEMARK OFFICE
CERTIFICATE OF CORRECTION

PATENT NO. : 5,424,187
DATED : June 13, 1995
INVENTOR(S) : A. Shor et al.

It is certified that error appears in the above-indentified patent and that said Letters Patent is hereby corrected as shown below:

| COLUMN | LINE | |
|---|---|---|
| 25 | 64-65 | "3)immunocytochemical" should read --3) immunocytochemical-- |
| 28 | 18 | "tiler" should read --titer-- |
| 30 | 33 | "lipid).." should read --lipid).-- |

Signed and Sealed this

Thirty-first Day of October 1995

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES:3

( 2 ) INFORMATION FOR SEQ ID NO:1:

( i ) SEQUENCE CHARACTERISTICS:
        ( A ) LENGTH:851 base pairs
        ( B ) TYPE:nucleic acid
        ( C ) STRANDEDNESS:single
        ( D ) TOPOLOGY:linear ( i i ) MOLECULE TYPE:genomic DNA
        ( A ) DESCRIPTION:Case 7

( i x ) SEQUENCE DESCRIPTION: SEQ ID NO:1:

```
GTGTAATTAG  GCATCTAATA  TATATTAAAG  AAGGGGATCT  TCGGACCTTT  CGGTTGAGGA    60
AGAGTTTATG  CGATATCAGC  TTGTTGGTGG  GGTAAAAGCC  CACCAAGGCG  ATGACGTCTA   120
GGCGGATTGA  GAGATTGACC  GCCAACACTG  GGACTGAGAC  ACTGCCCAGA  CTTCTACGGG   180
AGGCTGCAGT  CGAGAATCTT  TCGCAATGGA  CGAAAGTCTG  ACGAAGCGGC  GCCGCGTGTG   240
TGATGAAGGC  CTTAGGGTTG  TAAAGCACTT  TCGCCTGGGA  ATAAGAGAGA  TTGGCTAATA   300
TCCAATCGAT  TTGAGCGTAC  CGGGTAAAGA  AGCACCGGCT  AACTCCGTGC  CAGCAGCTGC   360
GGTAATACGG  AGGGTGCTAG  CGTTAATCGG  ATTTATTGGG  CGTAAAGGGC  GTGTAGGCGG   420
AAAGGAAAGT  TAGATGTTAA  ATTTTGGGGC  TCAACCCCAA  GTCAGCATTT  AAAACTATCT   480
TTCTAGAGGA  TAGATGGGGA  AAAGGGAATT  CCACGTGTAG  CGGTGAAATG  CGTAGATATG   540
TGGAAGAACA  CCAGTGGCGA  AGGCGCTTTT  CTAATTTATA  CCTGACGCTA  AGGCGCGAAA   600
GCAAGGGGAG  CAAACAGGAT  TAGATACCCT  GGTAGTCCTT  GCCGTAAACG  ATGCATACTT   660
GATGTGGATG  GTCTCAACCC  CATCCGTGTC  GGAGCTAACG  TGTTAAGTAT  GCCGCCTGAG   720
GAGTACACTC  GCAAGGGTGA  AACTCAAAAG  GATTGACGGG  GGCCCGCACA  AGCAGTGGAG   780
CATGTGGTTT  AATTCGATGC  AACGCGAAGG  ACCTTACCTG  GACTTGACAT  GTATTTGACA   840
ACTGTAGAAA  T                                                           851
```

( 2 ) INFORMATION FOR SEQ ID NO:2:

( i ) SEQUENCE CHARACTERISTICS:

(A) LENGTH:851 base pairs
(B) TYPE:nucleic acid
(C) STRANDEDNESS:single
(D) TOPOLOGY:linear (ii) MOLECULE TYPE:genomic DNA
(A) DESCRIPTION:Cpn (ix) SEQUENCE DESCRIPTION: SEQ ID NO:2:

| | | | | | | |
|---|---|---|---|---|---|---|
| GTGTAATTAG | GCATCTAATA | TATATTAAAG | AAGGGGATCT | TCGGACCTTT | CGGTTGAGGA | 60 |
| AGAGTTTATG | CGATATCAGC | TTGTTGGTGG | GGTAAAAGCC | CACCAAGGCG | ATGACGTCTA | 120 |
| GGCGGATTGA | GAGATTGACC | GCCAACACTG | GGACTGAGAC | ACTGCCCAGA | CTTCTACGGG | 180 |
| AGGCTGCAGT | CGAGAATCTT | TCGCAATGGA | CGAAAGTCTG | ACGAAGCGGC | GCCGCGTGTG | 240 |
| TGATGAAGGC | CTTAGGGTTG | TAAAGCACTT | TCGCCTGGGA | ATAAGAGAGA | TTGGCTAATA | 300 |
| TCCAATCGAT | TTGAGCGTAC | CGGGTAAAGA | AGCACCGGCT | AACTCCGTGC | CAGCAGCTGC | 360 |
| GGTAATACGG | AGGGTGCTAG | CGTTAATCGG | ATTTATTGGG | CGTAAAGGC | GTGTAGGCGG | 420 |
| AAAGGAAAGT | TAGATGTTAA | ATTTGGGGC | TCAACCCCAA | GTCAGCATTT | AAAACTATCT | 480 |
| TTCTAGAGGA | TAGATGGGGA | AAAGGGAATT | CCACGTGTAG | CGGTGAAATG | CGTAGATATG | 540 |
| TGGAAGAACA | CCAGTGGCGA | AGGCGCTTTT | CTAATTTATA | CCTGACGCTA | AGGCGCGAAA | 600 |
| GCAAGGGGAG | CAAACAGGAT | TAGATACCCT | GGTAGTCCTT | GCCGTAAACG | ATGCATACTT | 660 |
| GATGTGGATG | GTCTCAACCC | CATCCGTGTC | GGAGCTAACG | TGTTAAGTAT | GCCGCCTGAG | 720 |
| GAGTACACTC | GCAAGGGTGA | AACTCAAAAG | GATTGACGGG | GGCCCGCACA | AGCAGTGGAG | 780 |
| CATGTGGTTT | AATTCGATGC | AACGCGAAGG | ACCTTACCTG | GACTTGACAT | GTATTTGACA | 840 |
| ACTGTAGAAA | T | | | | | 851 |

(2) INFORMATION FOR SEQ ID NO:3:

(i) SEQUENCE CHARACTERISTICS:
(A) LENGTH:851 base pairs
(B) TYPE:nucleic acid
(C) STRANDEDNESS:single
(D) TOPOLOGY:linear (ii) MOLECULE TYPE:genomic DNA
(A) DESCRIPTION:Cps (ix) SEQUENCE DESCRIPTION: SEQ ID NO:3:

| | | | | | | |
|---|---|---|---|---|---|---|
| GTATGTTTAG | GCATCTAAAA | CATATTAAAG | AAGGGGATCT | TCGGACCTTT | CGGTTGAGGG | 60 |
| AGAGTCTATG | GGATATCAGC | TTGTTGGTGG | GGTAATGGCC | TACCAAGGCT | TGACGTCTA | 120 |
| GGCGGATTGA | GAGATTGACC | GCCAACACTG | GGACTGAGAC | ACTGCCCAGA | CTTCTACGGA | 180 |
| AGGCTGCAGT | CGAGAATCTT | TCGCAATGGA | CGAAAGTCTG | ACGAAGCGAC | GCCGCGTGTG | 240 |
| TGATGAAGGC | TCTAGGGTTG | TAAAGCACTT | TCGCTTGGGA | ATAAGAGAGA | TTGGCTAATA | 300 |
| TCCAATCGAT | TTGAGCGTAC | CAGGTAAAGA | AGCACCGGCT | AACTCCGTGC | CAGCAGCTGC | 360 |
| GGTAATACGG | AGGGTGCTAG | CGTTAATCGG | ATTTATTGGG | CGTAAAGGGC | GTGTAGGCGG | 420 |
| AAAGGAAAGT | TAGATGTTAA | ATCTTGGGGC | TCAACCCCAA | GCCAGCATCT | AATACTATCT | 480 |
| TTCTAGAGGG | TAGATGGAGA | AAAGGGAATT | CCACGTGTAG | CGGTGAAATG | CGTAGATATG | 540 |
| TGGAAGAACA | CCAGTGGCGA | AGGCGCTTTT | CTAATTTACA | CCTGACGCTA | AGGCGCGAAA | 600 |
| GCAAGGGGAG | CAAACAGGAT | TAGATACCCT | GGTAGTCCTT | GCCGTAAACG | ATGCATACTT | 660 |
| GATGTGGATA | GTCTCAACCC | TATCCGTGTC | GTAGCTAACG | CGTTAAGTAT | GCCGCCTGAG | 720 |
| GAGTACACTC | GCAAGGGTGA | AACTCAAAAG | AATTGACGGG | GGCCCGCACA | AGCAGTGGAG | 780 |
| CATGTGGTTT | AATTCGATGC | AACGCGAAGA | ACCTTACCTG | GCTTGACAT | GTATTTGACC | 840 |

GCGGCAGAAA T 851